(12) United States Patent
Garcia et al.

(10) Patent No.: US 10,918,428 B2
(45) Date of Patent: Feb. 16, 2021

(54) THORACIC PLATE IMPLANTS AND METHODS OF USE

(71) Applicant: Zimmer Biomet CMF and Thoracic, LLC, Jacksonville, FL (US)

(72) Inventors: Saddy Garcia, St. Augustine, FL (US); Jayden Garfield, Jacksonville, FL (US); Kevin Lee Teston, Jacksonville, FL (US); William Maxson, Ponte Vedra, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 0 days.

(21) Appl. No.: 16/183,141

(22) Filed: Nov. 7, 2018

(65) Prior Publication Data
US 2019/0142485 A1 May 16, 2019

Related U.S. Application Data

(60) Provisional application No. 62/585,050, filed on Nov. 13, 2017.

(51) Int. Cl.
*A61B 17/80* (2006.01)
*A61B 17/17* (2006.01)
*A61B 17/68* (2006.01)

(52) U.S. Cl.
CPC ...... *A61B 17/8076* (2013.01); *A61B 17/1792* (2016.11); *A61B 17/808* (2013.01); *A61B 17/8057* (2013.01); *A61B 2017/681* (2013.01)

(58) Field of Classification Search
CPC ... A61B 17/8076; A61B 17/84; A61B 17/842; A61B 17/82; A61B 17/823;
(Continued)

(56) References Cited

U.S. PATENT DOCUMENTS 5,607,430 A * 3/1997 Bailey .................. A61B 17/842
606/74
8,568,417 B2 10/2013 Petrzelka et al.
(Continued)

FOREIGN PATENT DOCUMENTS

JP 2001511678 A 8/2001
JP 2005524472 A 8/2005
(Continued)

OTHER PUBLICATIONS

"International Application Serial No. PCT US2018 059606, Written Opinion dated Feb. 19, 2019", 7 pgs.
(Continued)

*Primary Examiner* — Matthew J Lawson
*Assistant Examiner* — Lisa Nguyen
(74) *Attorney, Agent, or Firm* — Schwegman Lundberg & Woessner, P.A.

(57) ABSTRACT

An implant for a human rib can include an elongate body, a plurality of bores, and a placement tool interface. The elongate body can include a first portion including a flat outer face where the elongate body can be curved along a plane perpendicular to the flat outer face. The second portion can extend from the first portion to form a curved outer face. The plurality of bores can extend through the flat outer face of the first portion and into the second portion. The bores can extend partially into the curved outer face of the second portion. The placement tool interface can extend into the body.

17 Claims, 21 Drawing Sheets

(58) Field of Classification Search
CPC . A61B 17/826; A61B 17/808; A61B 17/8085; A61B 17/8057; A61B 17/1792; A61B 17/1796; A61B 17/1789
See application file for complete search history.

(56) References Cited

U.S. PATENT DOCUMENTS

| | | | |
|---|---|---|---|
| 8,702,719 B2* | 4/2014 | Refai | A61F 2/4611 |
| | | | 606/99 |
| 8,728,133 B2 | 5/2014 | Fell et al. | |
| 9,011,450 B2 | 4/2015 | Reichen et al. | |
| 9,060,809 B2* | 6/2015 | Tipimeni | A61B 17/685 |
| 9,603,642 B2 | 3/2017 | Fell et al. | |
| 10,463,411 B2* | 11/2019 | Knoepfle | A61B 17/1728 |
| 2010/0331892 A1 | 12/2010 | Fell et al. | |
| 2011/0184414 A1* | 7/2011 | Andermahr | A61B 17/809 |
| | | | 606/70 |
| 2013/0289564 A1* | 10/2013 | Bernstein | A61B 17/82 |
| | | | 606/74 |
| 2014/0277175 A1 | 9/2014 | Campbell et al. | |
| 2015/0100094 A1 | 4/2015 | Milz et al. | |
| 2016/0354126 A1 | 12/2016 | Nayet et al. | |

FOREIGN PATENT DOCUMENTS

| | | |
|---|---|---|
| WO | 2013049849 | 4/2013 |
| WO | WO-2013049849 A2 | 4/2013 |
| WO | 2017157802 | 9/2017 |
| WO | WO-2017157802 A1 | 9/2017 |
| WO | WO-2019094455 A1 | 5/2019 |

OTHER PUBLICATIONS

"International Application Serial No. PCT US2018 059606, International Search Report dated Feb. 19, 2019", 6 pgs.

"International Application Serial No. PCT/US2018/059606, International Preliminary Report on Patentability dated May 28, 2020", 9 pgs.

"Japanese Application Serial No. 2020-526210, Notification of Reasons for Refusal dated Nov. 17, 2020", with English translation, 8 pages.

\* cited by examiner

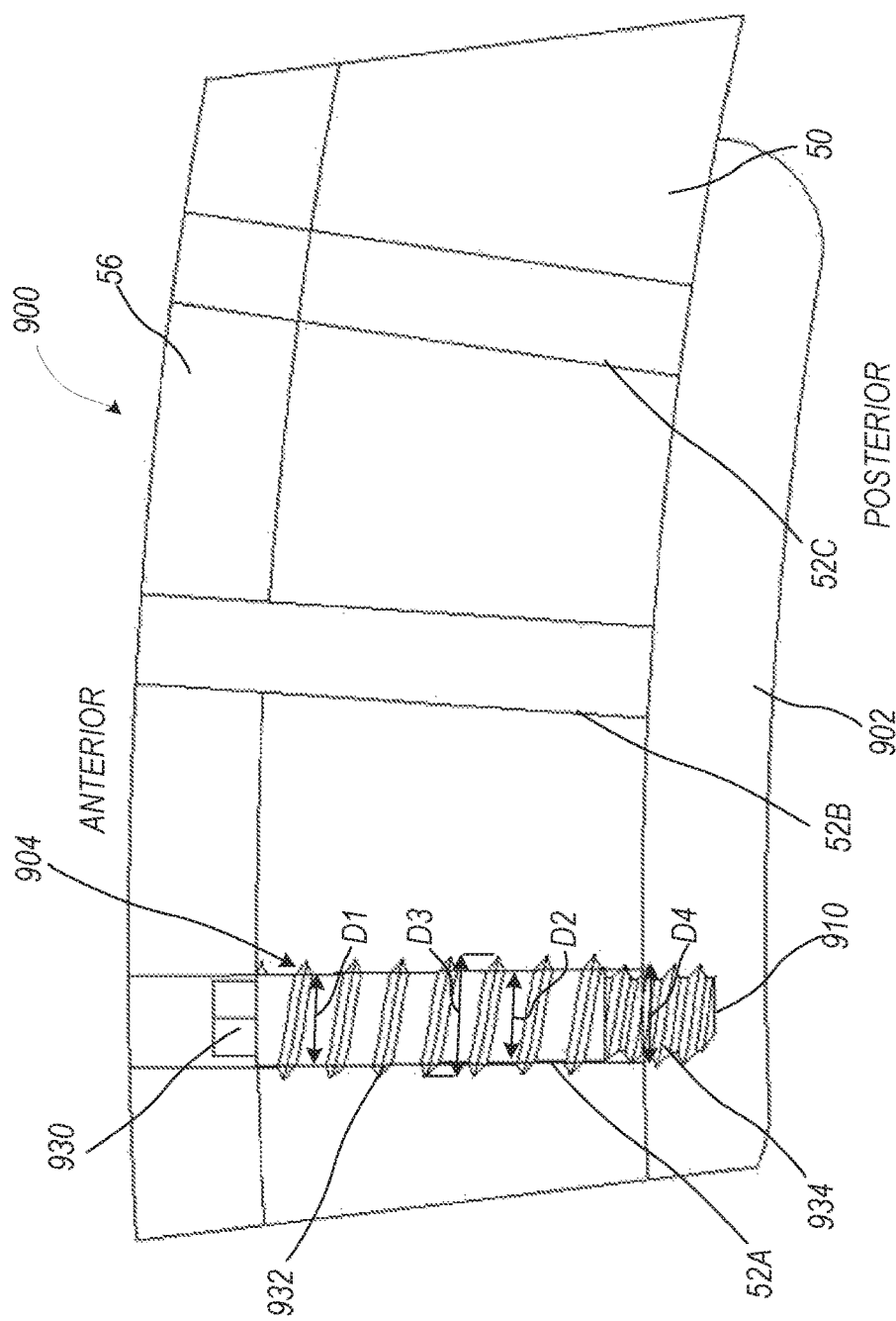

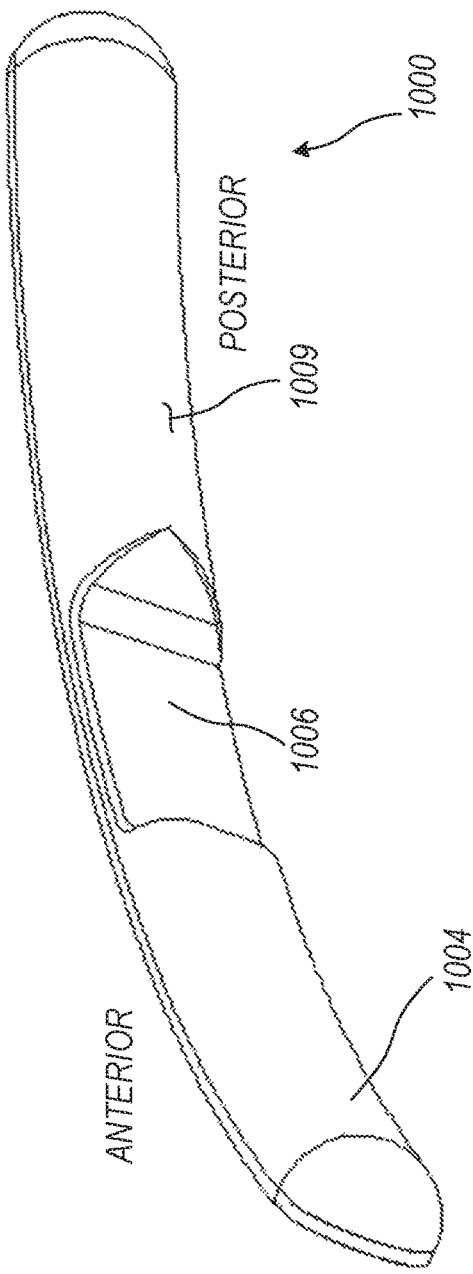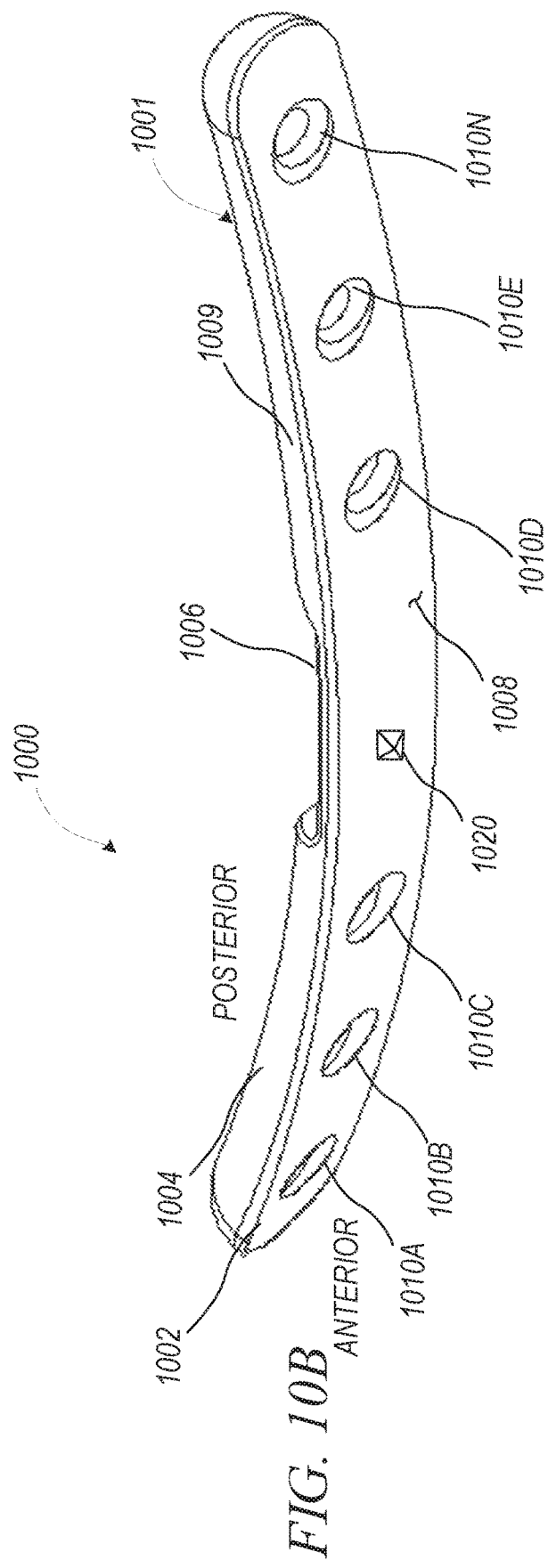
FIG. 10A
FIG. 10B

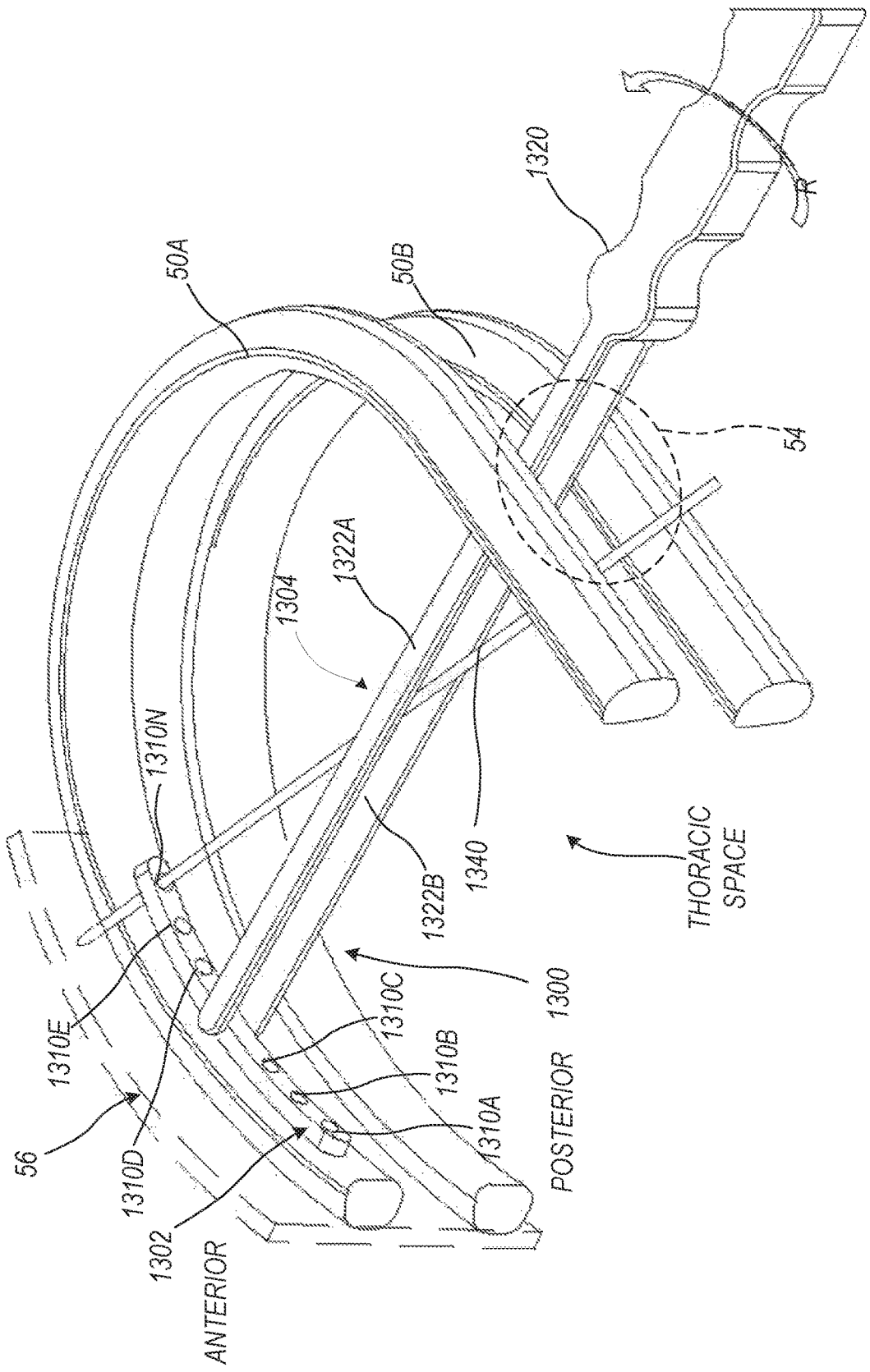

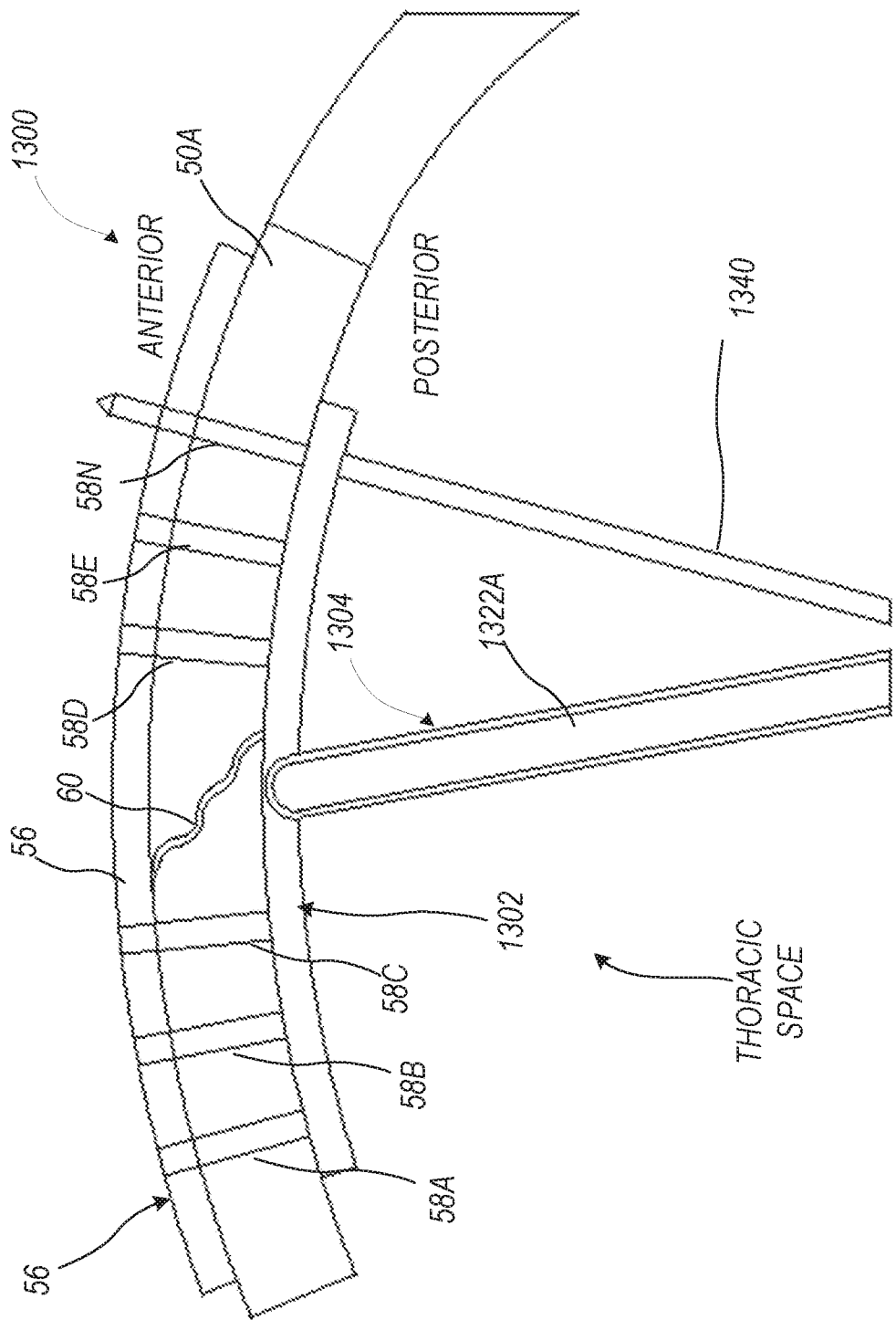

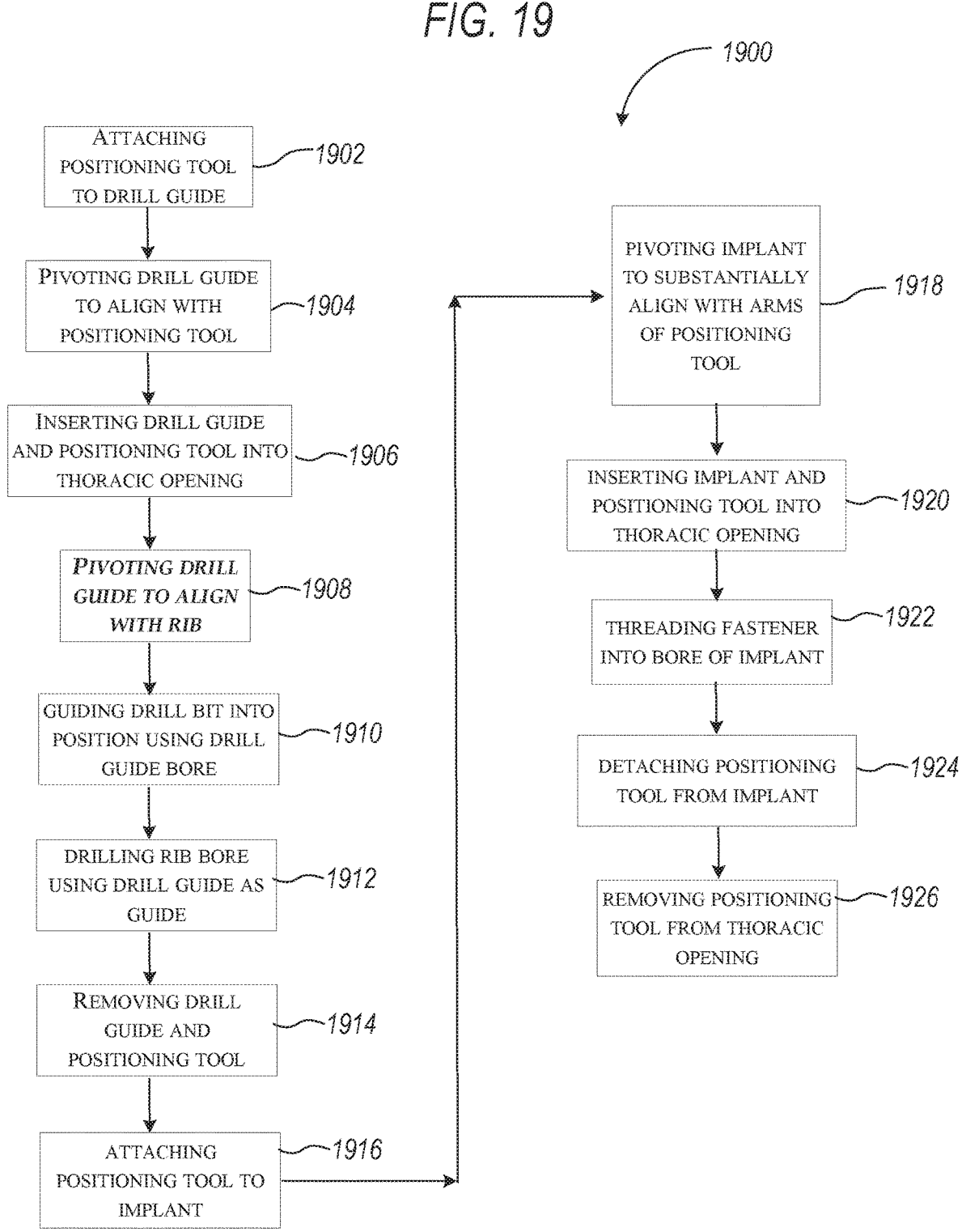

THORACIC PLATE IMPLANTS AND METHODS OF USE

CLAIM OF PRIORITY

This application claims the benefit of U.S. Provisional Patent Application Ser. No. 62/585,050, filed on Nov. 13, 2017, the benefit of priority of which is claimed hereby, and which is incorporated by reference herein in its entirety.

BACKGROUND

Implants are common in the medical field for strengthening bones of patients. In some cases, implants can be attachable to bones that are broken. For example, when patients have cracked and broken (fractured) ribs, surgeons sometimes install a plate to maintain rib alignment to promote proper healing. The plate can be secured to the rib on both sides of the fracture to maintain proper alignment of the rib during healing. The plate can be secured to the rib using fasteners. In some cases, the plate and fasteners can be removed from the patient after the fracture has healed.

OVERVIEW

In some cases of fractured ribs where a plate is required to promote proper healing, it may be desired to install the plate on the posterior portion of the rib for reduced palpability and increased comfort. In these cases, it is common to install the plate from the opposite side of the thoracic cavity. For example, a rib that is fractured at a ventral portion may be accessed from a posterior side of the patient. While this placement of an implant has many relative benefits, a procedure to place an implant as such can present several difficulties. For example, aligning the rib plate on the fractured rib and maintaining alignment for creation of bores in the rib and for fastening the plate to the rib can be a difficult process.

The present inventors have recognized, among other things, that a suture can be connected to the plate and pulled through a bore in the rib to align the plate to the rib for fastening, thereby improving the alignment and fastening process. The inventors have also recognized that a rib plate secured to the posterior portion of the fractured rib can include a curved anterior portion to reduce aggravation of adjacent tissues, where a template can be used in some examples to create bores for fastening the (posterior) rib plate from an anterior side of the rib. The rib plate can further include an interface for temporary connection to a placement tool, where the tool can be used to position the implant during drilling and fastening operations.

To further illustrate the apparatuses and systems disclosed herein, the following non-limiting examples are provided:

Example 1 is an implant for a human rib, the implant comprising: an elongate body comprising: a first portion including a flat outer face, the elongate body curved along a plane perpendicular to the flat outer face; and a second portion extending from the first portion to form a curved outer face; a plurality of bores extending through the flat outer face of the first portion and into the second portion; and a placement tool interface extending into the body.

In Example 2, the subject matter of Example 1 optionally includes wherein the placement tool interface comprises: a first bore extending into the second portion, the first bore configured to receive a placement tool.

In Example 3, the subject matter of Example 2 optionally includes wherein the placement tool interface comprises: a second bore coaxial with the first bore and configured to receive the placement tool.

In Example 4, the subject matter of Example 3 optionally includes wherein the first bore and second bore terminate in the second portion prior to intersecting.

In Example 5, the subject matter of any one or more of Examples 1-4 optionally include wherein the second portion comprises a notch in the curved face, configured to allow the elongate body to be bent at the notch.

In Example 6, the subject matter of Example 5 optionally includes wherein notch is located at the placement tool interface.

In Example 7, the subject matter of any one or more of Examples 1-6 optionally include wherein the flat outer face and the curved outer face form a half-capsule shape.

In Example 8, the subject matter of any one or more of Examples 1-7 optionally include wherein the body is curved to engage an interior rib surface.

In Example 9, the subject matter of any one or more of Examples 1-8 optionally include wherein the flat outer face comprises: a protrusion extendable into the human rib, the protrusion configured to limit movement of the flat outer face relative to the human rib when extended into the human rib.

Example 10 is an implant assembly for securing an implant to a human rib, the implant assembly comprising: an implant securable a human rib, the implant comprising: an elongate body comprising: a first portion and a second portion opposite the first portion; an implant bore extending through the first portion and partially into the second portion; and a placement tool interface extending into the body; a placement tool comprising: a handle; an arm extending from the handle; and a retaining pin extending from a distal portion of the arm, the retaining pin engageable with the placement tool interface to form a pivotable engagement therewith; and a fastener comprising: a proximal threaded portion securable to the rib; and a distal threaded portion extending distally from the proximal threaded portion, the distal threaded portion threadably securable to the implant bore.

In Example 11, the subject matter of Example 10 optionally includes the assembly further comprising: a lag screw configured to pass through a rib bore without threadably engaging the rib bore and including a lag distal threaded portion threadably securable to a second bore of the implant.

In Example 12, the subject matter of any one or more of Examples 10-11 optionally include wherein the fastener further comprises: a head comprising a tool interface, the head including a head diameter; and a body extending distally from the head, the body comprising: the proximal threaded portion that extends distally from the head, the proximal threaded portion comprising: a proximal minor diameter that is larger than the head diameter; and a proximal major diameter; and the distal threaded portion that extends distally from the proximal threaded portion, the distal threaded portion comprising: a distal major diameter of a size equal to or smaller than the proximal minor diameter.

In Example 13, the subject matter of Example 12 optionally includes wherein the distal threaded portion further comprises: a locking thread adjacent the proximal threaded portion, the locking thread configured to lockably engage one of the implant bore including a first thread type.

In Example 14, the subject matter of Example 13 optionally includes wherein the placement tool further comprises:

a second arm flexibly coupled to a distal portion of the elongate handle, the first and second arms extending distally from the elongate handle, the first and second arms movable between a first position and a second position.

In Example 15, the subject matter of Example 14 optionally includes wherein the placement tool further comprises: a second retaining pin extending from a distal portion of the second arm towards the first arm such that the first retaining pin is spaced away from the second retaining pin, the second retaining pin coaxial with the first retaining pin when the first and second arms are in a first position, the first retaining pin and second retaining pin spaced further apart when the first and second arms are in a second position.

In Example 16, the subject matter of Example 15 optionally includes wherein the placement tool interface further comprises: a first pin bore extending into the second portion, the first bore configured to receive the first retaining pin; and a second pin bore coaxial with the first pin bore and configured to receive the second retaining pin.

In Example 17, the subject matter of Example 16 optionally includes wherein the first pin bore and second pin bore terminate in the second portion prior to intersecting.

In Example 18, the subject matter of any one or more of Examples 10-17 optionally include wherein: the first portion includes a flat outer face, the elongate body curved along a plane perpendicular to the flat outer face; and the second portion extends from the first portion to form a curved outer face.

In Example 19, the subject matter of Example 18 optionally includes wherein the implant further comprises: a plurality of bores extending through the flat outer face and partially into the second portion, each of the plurality of bores capable of receiving the fastener.

In Example 20, the subject matter of any one or more of Examples 18-19 optionally include the second portion further comprising: a notch in the curved outer face located at the placement tool interface and configured to allow the elongate body to be bent at the notch.

Example 21 is a fastener for securing an implant to human bone, the fastener comprising: a head comprising a tool interface, the head including a head diameter; a body extending distally from the head, the body comprising: a proximal threaded portion extending distally from the head, the proximal threaded portion comprising: a proximal minor diameter that is larger than the head diameter; and a proximal major diameter; and a distal threaded portion extending distally from the proximal threaded portion, the distal threaded portion comprising: a distal major diameter of a size equal to or smaller than the proximal minor diameter.

In Example 22, the subject matter of Example 21 optionally includes the distal threaded portion further comprising thread configured to interface with a threaded bore and the proximal threaded portion further comprising thread configured to interface with bone.

In Example 23, the subject matter of any one or more of Examples 21-22 optionally include the distal threaded portion further comprising: a locking thread adjacent the proximal threaded portion, the locking thread configured to lockably engage an implant bore.

In Example 24, the subject matter of any one or more of Examples 21-23 optionally include wherein the proximal threaded portion includes self-tapping threads.

Example 25 is a placement tool for placing and securing an implant to human bone, the placement tool comprising: an elongate handle; first and second arms flexibly coupled to a distal portion of the elongate handle, the first and second arms extending distally from the elongate handle, the first and second arms movable between a first position and a second position; a first retaining pin extending from a distal portion of the first arm towards the second arm; and a second retaining pin extending from a distal portion of the second arm towards the first arm such that the first retaining pin is spaced away from the second retaining pin, the second retaining pin coaxial with the first retaining pin when the first and second arms are in the first position, the first retaining pin and second retaining pin spaced further apart when the first and second arms are in the second position.

In Example 26, the subject matter of Example 25 optionally includes a coupler engageable with the retaining pins and including a set of jaws coupleable to a recessed portion of a plate.

In Example 27, the subject matter of any one or more of Examples 25-26 optionally include wherein the first arm and the second arm are biased to the first position.

In Example 28, the subject matter of any one or more of Examples 25-27 optionally include wherein the first retaining pin and second retaining pin are configured to form a pivotable engagement with a placement tool interface of an implant when the arms are in the first position.

Example 29 is a method of securing an implant to human bone, the method comprising: creating a bore proximate a break in the human bone; passing a suture through first and second bores of an implant; passing the suture through the bore of the human bone; pulling the implant to an anterior portion of the human bone using the sutures; passing a fastener through a third bore of the implant; threading the fastener into the human bone with a distal thread of the fastener; and threading the fastener into the third bore of the implant with a proximal thread of the fastener.

In Example 30, the subject matter of Example 29 optionally includes removing the suture from the implant.

Example 31 is a method of securing an implant to human bone, the method comprising: attaching a drill guide to a placement tool; pivoting the drill guide to substantially align with arms of the placement tool; inserting the drill guide and the placement tool into a thoracic opening; pivoting the drill guide to align with a posterior portion of a rib; guiding a drill bit into position using a drill guide bore; drilling a rib bore using the drill guide bore as a guide; removing the drill guide and the placement tool from the thoracic opening; attaching the placement tool to an implant; pivoting the implant to substantially align with arms of the placement tool; inserting the implant and the placement tool into a thoracic opening; and threading the fastener into a bore of the implant with a distal thread of the fastener.

In Example 32, the subject matter of Example 31 optionally includes detaching the placement tool from the implant; and removing the placement tool from the thoracic opening.

In Example 33, the subject matter of any one or more of Examples 31-32 optionally include continuing drilling through skin adjacent the rib bore.

In Example 34, the implant, assembly, or method of any one of or any combination of Examples 1-34 is optionally configured such that all elements or options recited are available to use or select from.

These and other examples and features of the present apparatuses and systems will be set forth in part in the following Detailed Description. This Overview is intended to provide non-limiting examples of the present subject matter and it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

FIG. 9A shows an isometric view of a fastener of an implant assembly, in accordance with an example of the present disclosure.

FIG. 9B shows an isometric view of an implant assembly, in accordance with an example of the present disclosure.

FIG. 10A shows a posterior isometric view of another implant, in accordance with an example of the present disclosure.

FIG. 10B shows an anterior isometric view of another implant, in accordance with an example of the present disclosure.

FIG. 14A shows an isometric view of a step of installing an implant assembly, in accordance with an example of the present disclosure.

FIG. 14B shows a top isometric view of the step of FIG. 14A of installing an implant assembly, in accordance with an example of the present disclosure.

FIG. 19 shows a flow chart of a surgical procedure performed using a rib and sternal implant and tool, in accordance with an example of the present disclosure.

DETAILED DESCRIPTION

The present application relates to devices and systems for orthopedic implant procedures. For example, the present application discloses a rib implant system configured to secure to a rib or ribs of a patient. The description below discusses rib implants primarily configured to engage an interior portion of a rib referred to as a posterior portion of the rib throughout the description. In some embodiments, these implants can be alternatively configured to engage the outer or anterior portion of a rib. Details are discussed further below.

Figure 1:
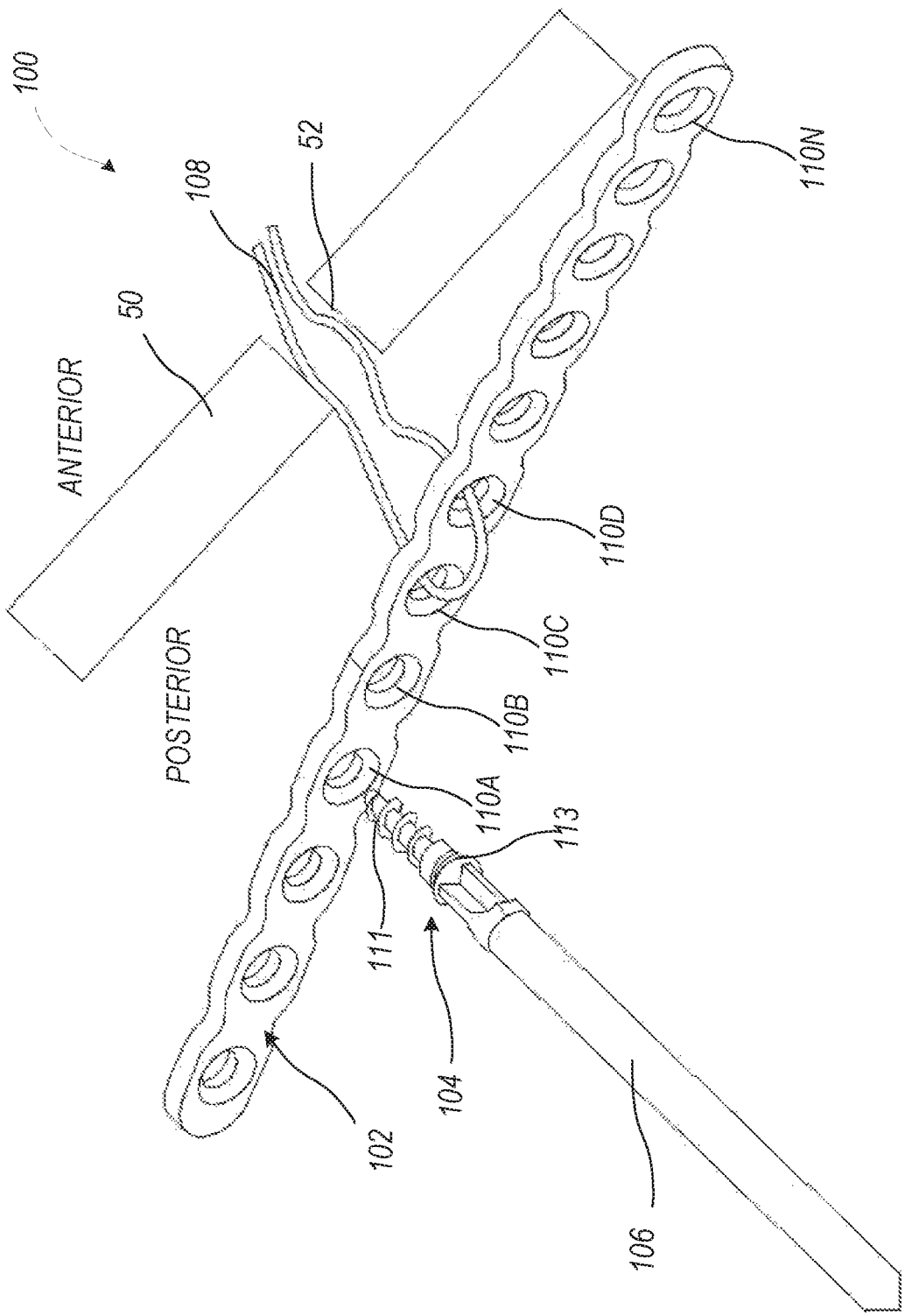
FIG. 1 shows an isometric view of a rib and an implant assembly, in accordance with an example of the present disclosure.

FIG. 1 shows an isometric view of implant assembly 100 and rib 50 of a patient, in accordance with an example of the present disclosure. Rib 50 can include rib bore 52. Implant assembly 100 can include implant 102, fastener 104, driver 106, and suture 108. Implant 102 can include implant bores 110A-110N. Fastener 104 can include distal threaded portion 111 and proximal threaded portion 113. FIG. 1 also shows orientation indicators Anterior and Posterior.

Implant 102 can be a rigid or semi-rigid member comprised of materials such as plastics, metals, composites, and the like. In some examples, implant 102 can be comprised of biocompatible metals and alloys such as stainless steel, titanium, and cobalt chromium. Implant 102 can include bores 110A-110N, which can be spaced apart, equally in some examples, along a length of a body of implant 102. Each of bores 110a-110n can be threaded to receive proximal threaded portion 113 of fastener 104.

Fasteners 104 can be rigid fasteners comprised of materials such as plastics, metals, composites, and the like. In some examples, fasteners 104 can be composed of biocompatible metals and alloys such as stainless steel, titanium, and cobalt chromium. Fasteners 104 can include proximal threaded portion 113 configured to secure to bores 110A-110N of implant 102 and distal threaded portion 111 configured to secure to bone (as discussed in more detail further below).

Driver 106 can be a driver such as a screw driver, configured to transfer a torque from a handle down a shaft and to the head of fastener 104. Driver 106 can include a fastener interface, such as standard, cross-recess, hex, and the like. Sutures 108 can be medical sutures composed of absorbable or non-absorbable materials such as nylon, polyester, polypropylene, polyamide, silk, steel, metallic strands, polyglactin, polyglycolic acid, catgut, poliglecaprone, polydioxanone, combinations thereof, and the like.

In some patients, rib 50 may be fractured due to trauma. In these cases, rib plate 102 can be secured to rib 50 to maintain alignment of the rib during the healing process. However, alignment of implant 102 with rib 50 can be difficult. In these cases, suture 108 can be passed through two or more of implant bores 110A-110N. As shown in FIG. 1, suture 108 can be passed through bores 110C and 110D.

Suture 108 can then be passed through bone bore 52 to an anterior side of rib 50. In other examples, suture 108 can be pre-mounted to implant 102 prior to the insertion of implant 102 into the thoracic space. Suture 108 can be pulled tight from an anterior side of rib 50, drawing implant 102 against a posterior side of rib 50. Holding suture 108 tight can hold implant 102 in place against rib 50 while bores are created in rib 50 using implant 102 as a template. Sutures 108 can be held tight until fasteners (such as fastener 104) are driven into the bores of rib 50 and have secured implant 102 to rib 50. After fasteners 104 have secured implant 102 to rib 50, sutures 108 can be left in place (if absorbable) or can be removed, and holes 110C and 110D (that were used for suture) can receive fasteners therethrough to further secure implant 102 to rib 50.

Figure 2:
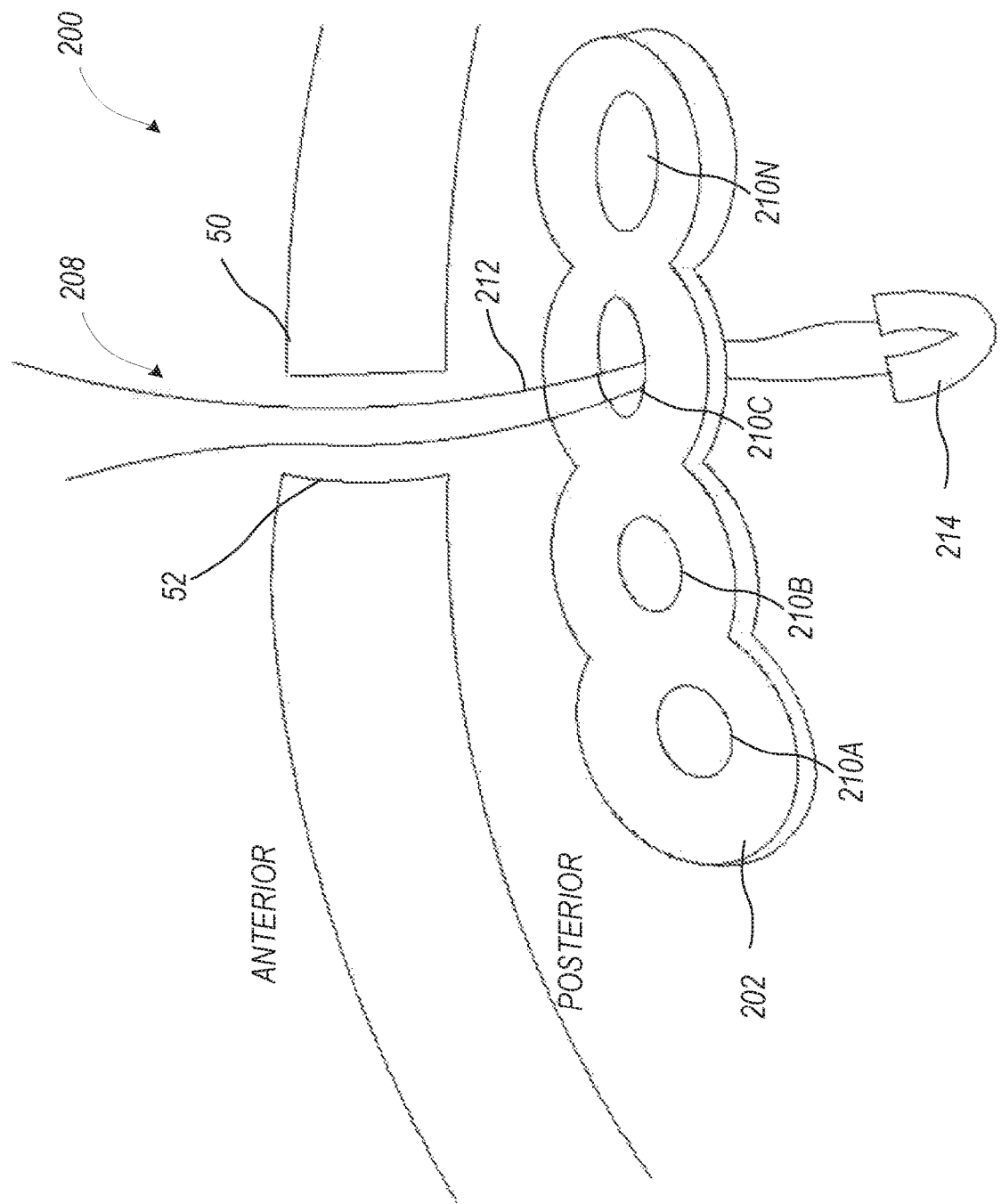
FIG. 2 shows an isometric view of a rib and another implant assembly, in accordance with an example of the present disclosure.

FIG. 2 shows an isometric view of implant assembly 200 and rib 50 of a patient, in accordance with an example of the present disclosure. Rib 50 can include rib bore 52. Implant assembly 200 can include implant 202 and suture 208. Implant 202 can include implant bores 210A-210N. FIG. 2 also shows orientation indicators Anterior and Posterior.

Implant assembly 200 can be similar to implant assembly 100 described above with respect to FIG. 1, except that implant assembly 100 can include suture 208, which can include line 212 and knot-up 214. Line 212 and knot-up 214 can be composed of materials described above with reference to sutures 108.

In operation of some examples, suture 208 can be passed through bore 210C. Suture 208 can then be passed through bone bore 52 to an anterior side of rib 50. Ends of suture 208 can be pulled tight causing knot-up 214 to change shape, creating a knot or dense portion of material that has a size larger than bore 210C such that knot-up 214 cannot pass through bore 210C. Suture 208 can then be pulled at an anterior side of rib 50, drawing implant 202 against a posterior side of rib 50. Holding suture 208 tight can hold implant in place so that bores can be created in rib 50 and so that fasteners (such as fastener 104 of FIG. 1) can be driven into the bores of the rib and secured to implant 202. Suture 208 can provide the benefit of only passing through a single bore, allowing that bore, such as bore 210C to be aligned with bore 52 of rib 50. This can reduce the number or size of required rib bores.

Figure 3:
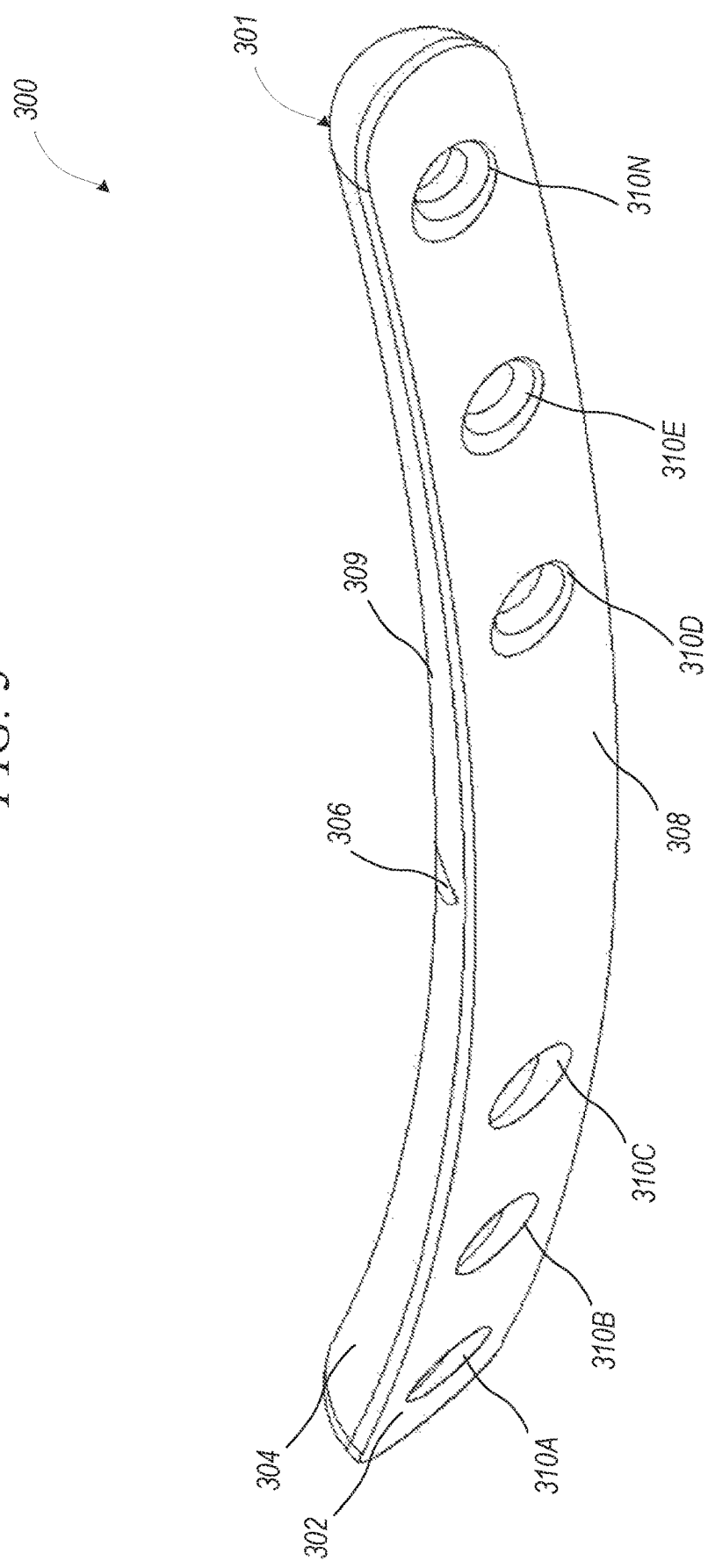
FIG. 3 shows an isometric view of an implant, in accordance with an example of the present disclosure.

FIG. 3 shows an isometric view of implant 300, in accordance with an example of the present disclosure. Implant 300 can include body 301, tool interface 306, and bores 310A-310N. Body 301 can include portion 302 and curved portion 304. Portion 302 can be flat in cross-section and rounded or curved along its length, as shown in FIG. 3. Edges of body 301 can be tapered and smooth to prevent soft tissue irritation.

Body 301 can be a rigid or semi-rigid member comprised of materials such as plastics, metals, composites, and the like. In some examples, body 301 can be comprised of biocompatible metals and alloys such as stainless steel, titanium, and cobalt chromium. Portion 302 of body 301 can include flat outer face 308. Curved portion 304 can extend from portion 302 to form curved outer face 309. In some examples, curved portion 304 can have a smooth exterior with rounded corners to limit friction between second portion 304 and surrounding tissue, limiting discomfort and reducing a possibility of puncturing or abrading of internal organs. In some examples, flat face 308 of portion 302 can have an abrasive surface configured to prevent movement of implant 300 relative to a rib. In other examples, flat face 308 of portion 302 can have a smooth surface configured to allow movement of implant 300 relative to a rib when, for example, a rib is likely to move during the healing process.

Bores 310A-310N can be threaded bores, in some examples, extending through flat outer face 308 of first portion 302 and into second portion 304. Tool interface 306 can be a bore or bores extending into body 301. In some examples, tool interface 306 can be a bore, slot, aperture, or other opening configured to receive a notch or protrusion of a tool. In some examples, tool interface 306 can have a round geometric shape, but can have other shapes in other examples. In some examples, tool interface 306 can be a single bore extending entirely through implant 300 configured to receive one or more portions of a tool. In other examples, tool interface 306 can be multiple bores, each configured to receive a portion of a tool. Operation of implant 300 is described with respect to FIGS. 5-9 and 13-19 below.

Figure 4A:
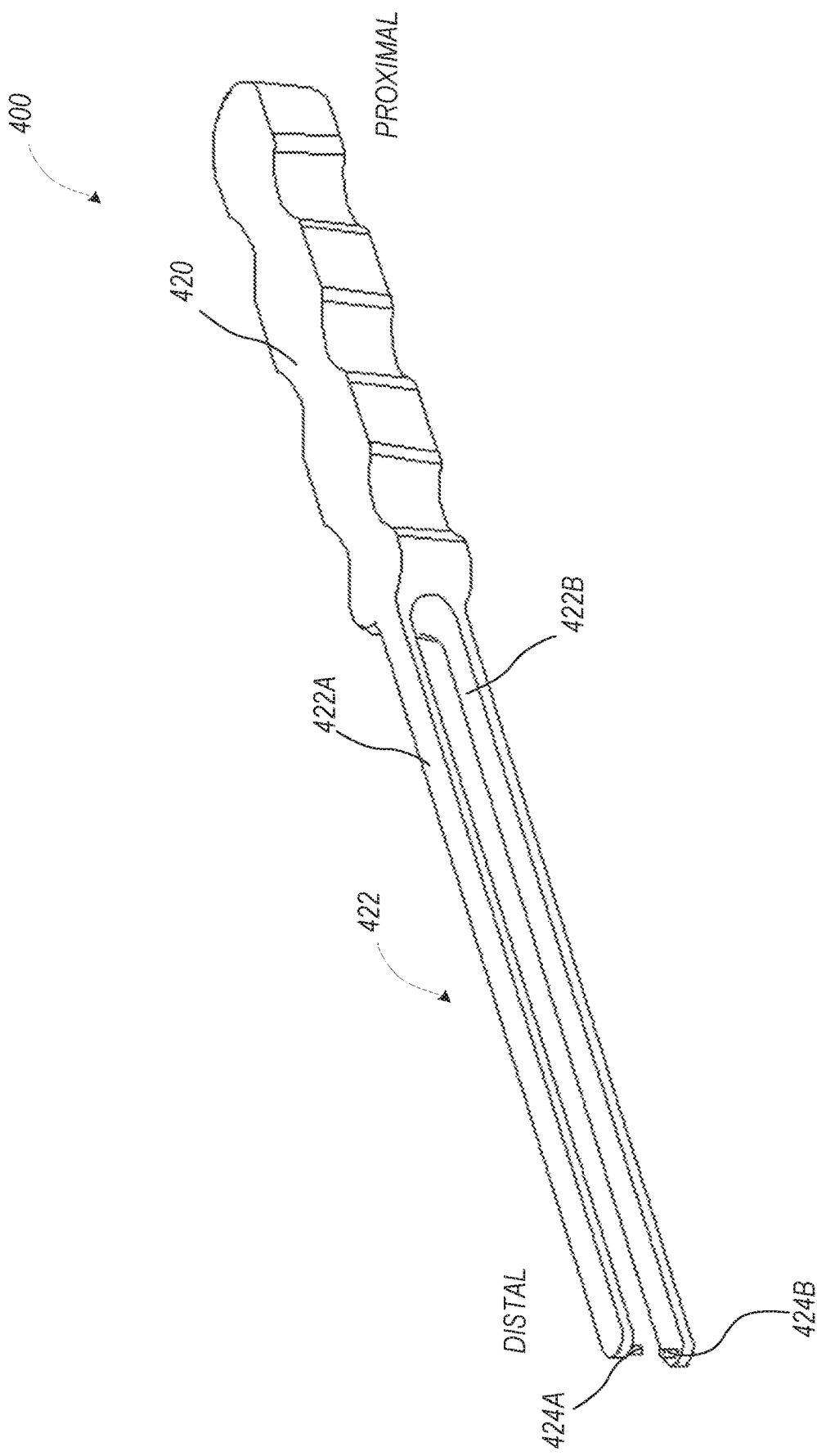
FIG. 4A shows an isometric view of a placement tool, in accordance with an example of the present disclosure.

FIG. 4A shows an isometric view of placement tool 400, in accordance with an example of the present disclosure. Placement tool 400 can include handle 420 and arms 422. FIG. 4A also shows orientation indicators Proximal and Distal.

Handle 420 and arms 422A and 422B can be rigid or semi-rigid members comprised of materials such as plastics, metals, composites, combinations thereof, and the like. Handle 420 can have a profile shaped for ergonomics and traction, in some examples. Arms 422A and 422B can extend from a distal portion of handle 420 generally parallel to each other. Arm 422A can include pin 424A (or retaining pin/first retaining pin) and arm 422B can include pin 424B (or second retaining pin). In some examples, pin 424A can extend from an inner surface of arm 422A generally perpendicular to arm 422A and toward arm 422B and pin 424B. Similarly, pin 424B can extend from an inner surface of arm 422B generally perpendicular to arm 422B and toward arm 422A and pin 424A. In some examples, pins 424A and 424B can be coaxial when arms 422A and 422B are parallel. In some other examples, arms 422 can include only one pin. Similarly, tool 400 can include only one arm 422 and one pin 424. In these examples, pin 424 can be relatively longer to extend entirely through a tool interface, in some examples.

In some examples, arms 422A and 422B can be cantilevered from handle 420, such that arms 422A and 422B can flexibly move toward and away from each other, allowing pins 424A and 424B to move toward and away from each other. Because arms 422 and body 420 can be comprised of rigid and semi-rigid materials, arms 422 can be attached to body 420 such that flexing of arms 422 at handle 420 allowing for relative movement of arms 422 can be within an elastic region of the materials of handle 420 and arms 422 allowing arms 422 to return to a parallel position when a force causing relative displacement of arms 422 is removed. Because arms 422A and 422B are parallel, they can create a low visibility profile, increasing visibility of a fracture site. Operation of placement tool 400 is described with respect to the FIGS. 5-9 and 13-19 below.

Figure 4B:
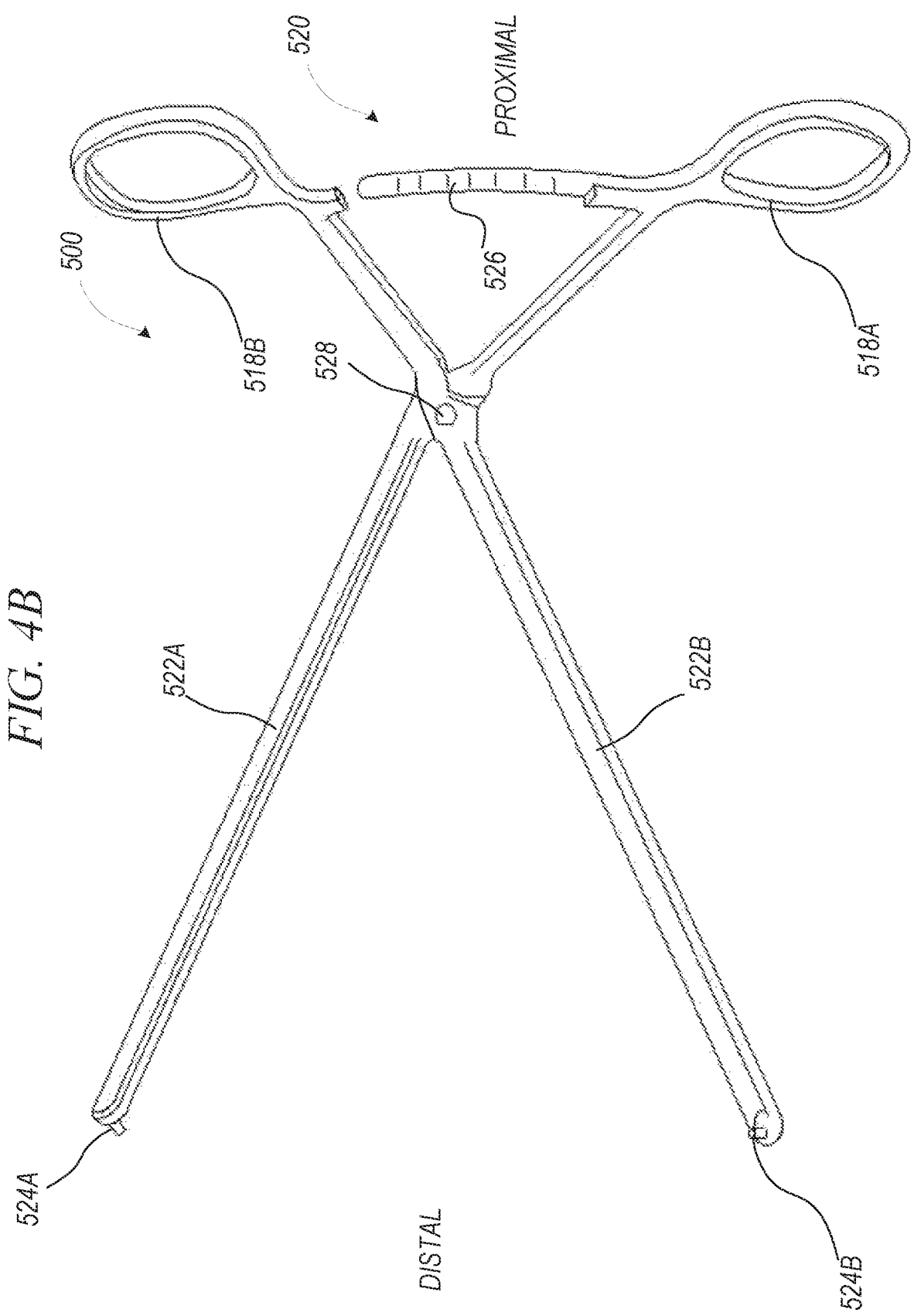
FIG. 4B shows an isometric view of a placement tool, in accordance with an example of the present disclosure.

FIG. 4B shows an isometric view of placement tool 500, in accordance with an example of the present disclosure. Placement tool 500 can be similar to placement tool 400, except that handle 520 of placement tool 500 can include finger holes 518A and 518B, locking interface 526 and pivot joint 528. Finger hole 518A can be coupled to arm 522A and finger hole 518B can be coupled to arm 522B. FIG. 4B also shows orientation indicators Proximal and Distal.

Arms 522A and 522B can be pivotably coupled at pivot joint 528 such that finger holes 518A and 518A can be operated in a scissor-like fashion to open and close arms 522A and 522B so that pins 524A and 524B can engage an implant. Locking device 526 can be a feature extending between arms 522A and 522B allowing for automatic locking and manual release of the arms 522A and 522B relative to each other, similar to the operation of Kelly forceps, in some examples.

Figure 5:
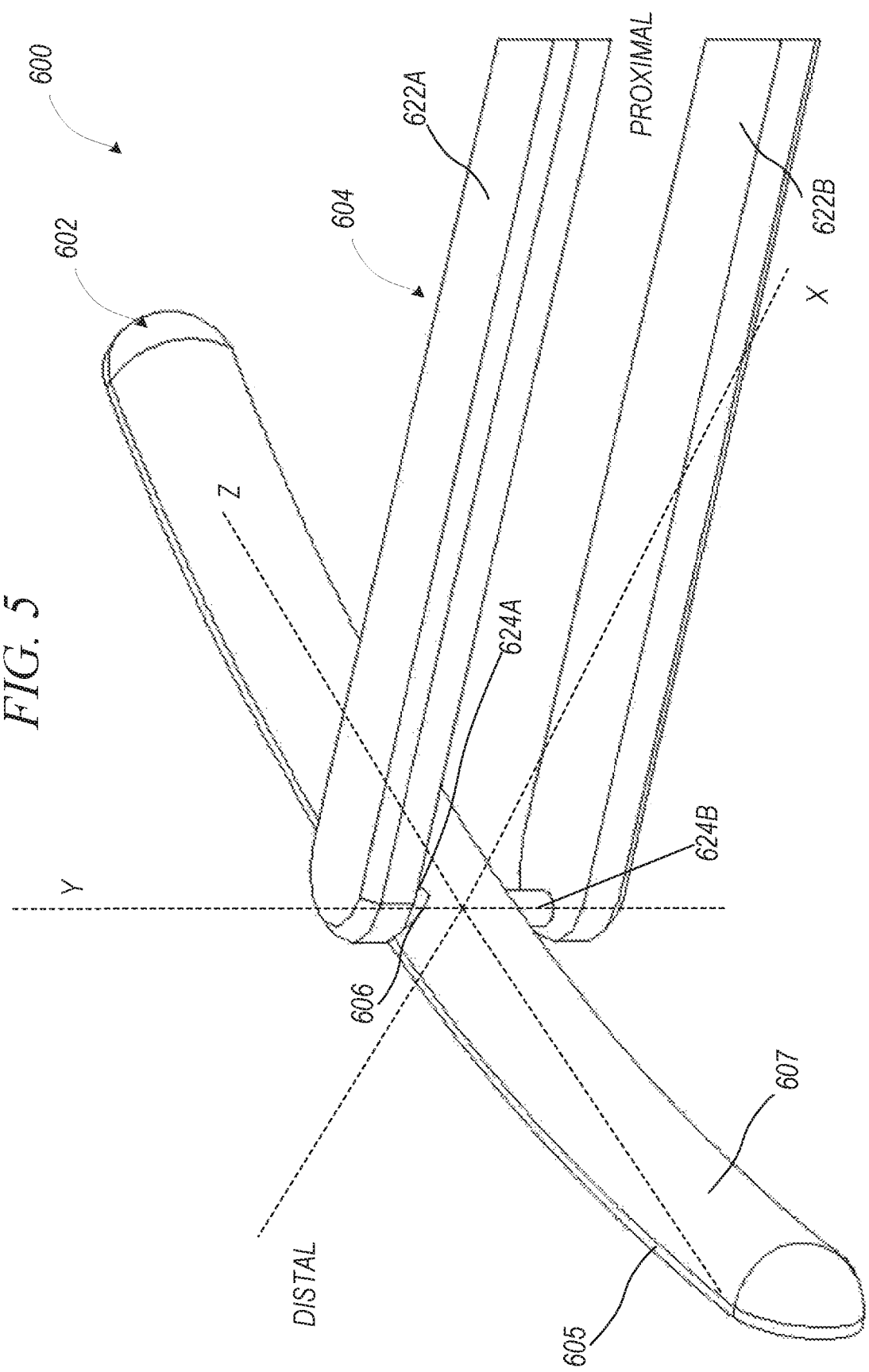
FIG. 5 shows an isometric view of an implant assembly, in accordance with an example of the present disclosure.
Figure 6:
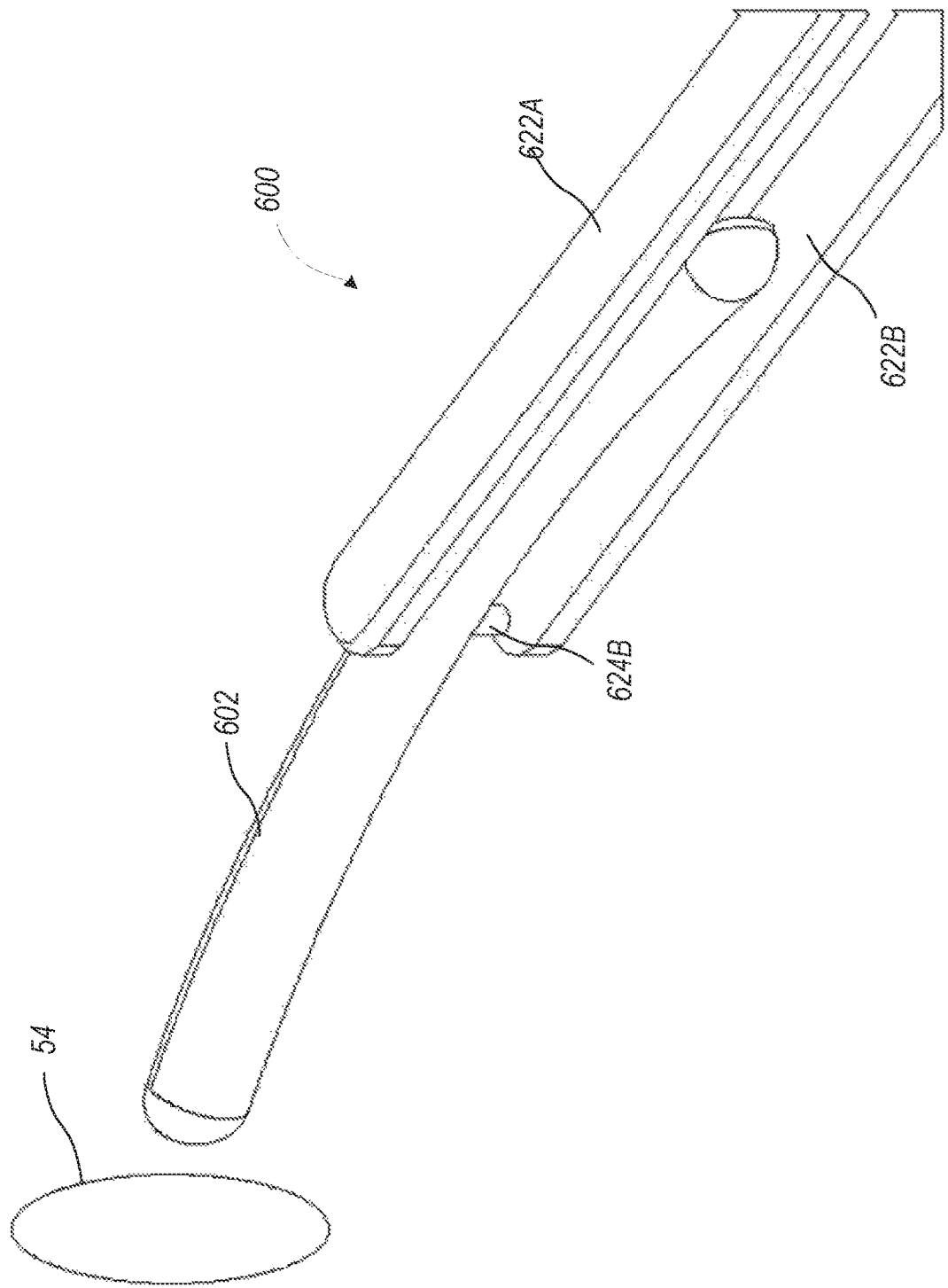
FIG. 6 shows an isometric view of the implant assembly of FIG. 5 in another configuration, in accordance with an example of the present disclosure.

FIG. 5 shows an isometric view of an implant assembly 600 in a first configuration, in accordance with an example of the present disclosure. FIG. 6 shows an isometric view of implant assembly 600 in another configuration, in accordance with an example of the present disclosure. FIGS. 5 and 6 are discussed below concurrently.

Implant assembly 600 can include implant 602 and implant tool 604. Implant 602 can include flat portion 605 and curved portion 607. Placement tool 604 can include arms 622A and 622B, which can include pins 624A and 624B, respectively. FIG. 5 also shows axes X, Y, and Z. FIG. 6 also shows orientation indicators Proximal and Distal.

Implant 602 can be similar to implant 300 described above with respect to FIG. 3 and placement tool 604 can be similar to either of placement tools 400 of FIG. 4A or 500 of FIG. 4B, except that FIG. 5 more clearly shows how implant 602 can be curved such that flat portion 605 and curved portion 607 can form a half-capsule shape of implant 602. In some examples, implant 602 can be curved along a plane formed by the Y and Z axes, substantially perpendicular to the flat face of flat portion 605. The curvature can be matched to patient-specific anatomy, in some examples. In other examples, the curvature can be matched to average curvature of ribs. In other examples, the curvature can be matched to average ribs of a specific anatomic location, such as true, floating, or false ribs. Further, the curvature can be matched to average ribs of a specific anatomic location, such as an anterior portion, a posterior portion, or a medial portion.

FIGS. 5 and 6 also illustrate how implant 602 and placement tool 604 can operate together, in some examples. As shown in FIG. 5, pins 624A and 624B can be inserted into tool interface 606. Once pins 624A and 624B are inserted into tool interface 606, implant 602 can be pivoted about pins 624a and 624b and therefore relative to arms 622A and 622B such that implant 602 can rotate entirely (360 degrees) between arms 622A and 622B. In some examples, placement tool 604 can include a stop to limit rotation past, for example, 190 degrees of rotation.

In one example, as shown in FIG. 5, implant 602 can be substantially perpendicular to arms 622A and 622B. Implant 602 can then be pivoted to be substantially parallel to (or in alignment with) arms 622A and 622B, as shown in FIG. 6. This can allow implant assembly 600 to be inserted into a relatively small incision.

For example, in the example shown in FIG. 6, implant 602 and arms 622A and 622B can be in alignment and can be inserted into thoracic opening 54. Once implant 602 and placement tool 604 have been fully inserted into a thoracic cavity, implant 602 can then be pivoted again such that implant 602 is substantially perpendicular to arms 622A and 622B (or any position in between parallel and perpendicular) to allow for securing of implant 602 to a rib, as discussed further below.

Figure 7:
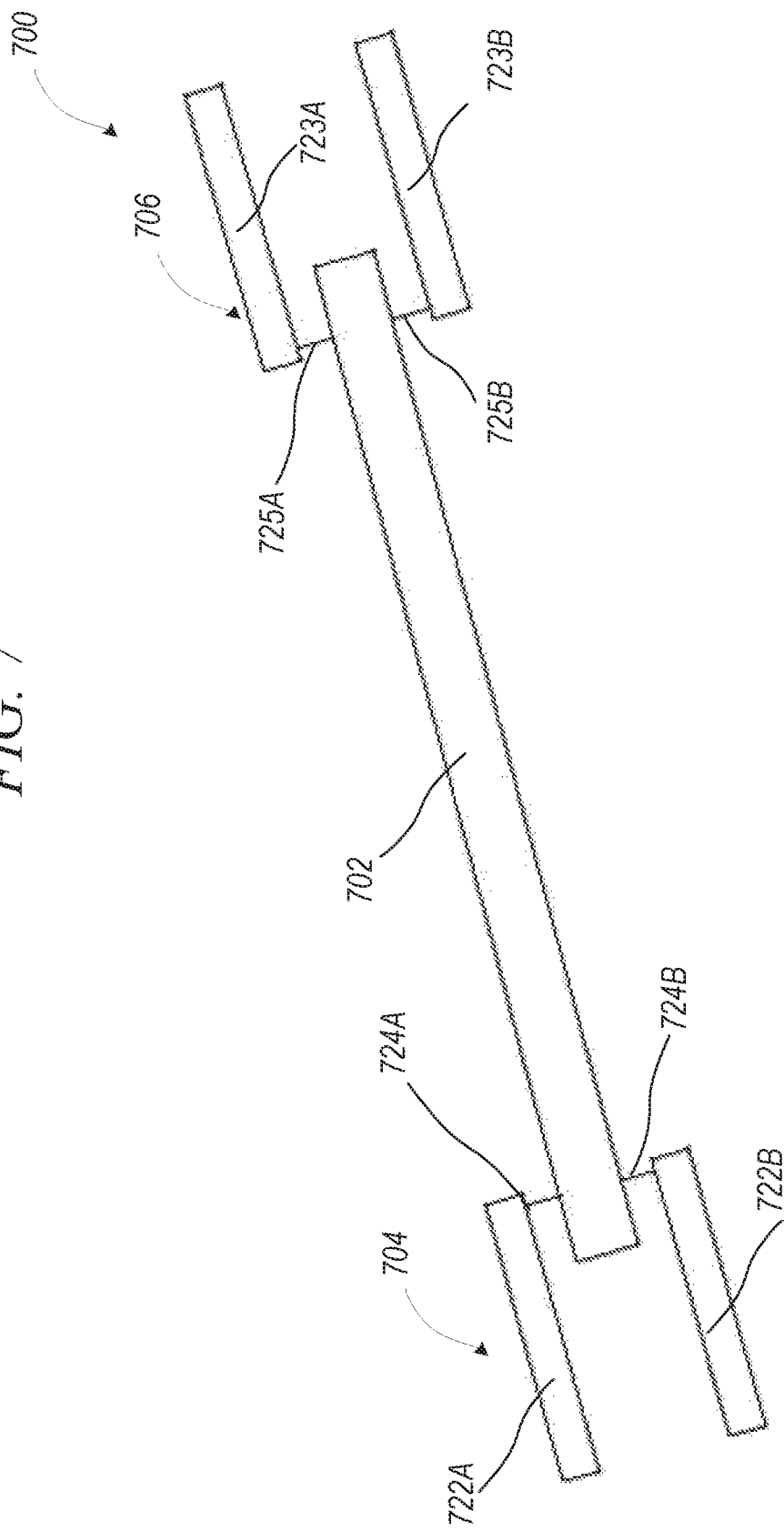
FIG. 7 shows an elevation view of another implant assembly, in accordance with an example of the present disclosure.

FIG. 7 shows an elevation view of implant assembly 700, in accordance with an example of the present disclosure. Implant assembly 700 can include implant 702, first placement tool 704, and second placement tool 706. First placement tool 704 can include arms 722A and 722B, each of which can include pins 724A and 724B. Second placement tool 706 can include arms 723A and 723B, each of which can include pins 725A and 725B.

In this example, multiple placement tools can be connected to implant 702 to place implant 702 within a thoracic cavity. Use of multiple placement tools, such as first placement tool 704 and second placement tool 706, can provide additional stability of implant 702 during placement, drilling, and fastening operations performed on implant 702 within a thoracic cavity. In some examples, placement tools 704 and 706 can be aligned with implant 702 to form an assembly having a narrow profile, allowing assembly 700 to pass through a relatively small incision opposite the rib to be repaired.

Figure 8B:
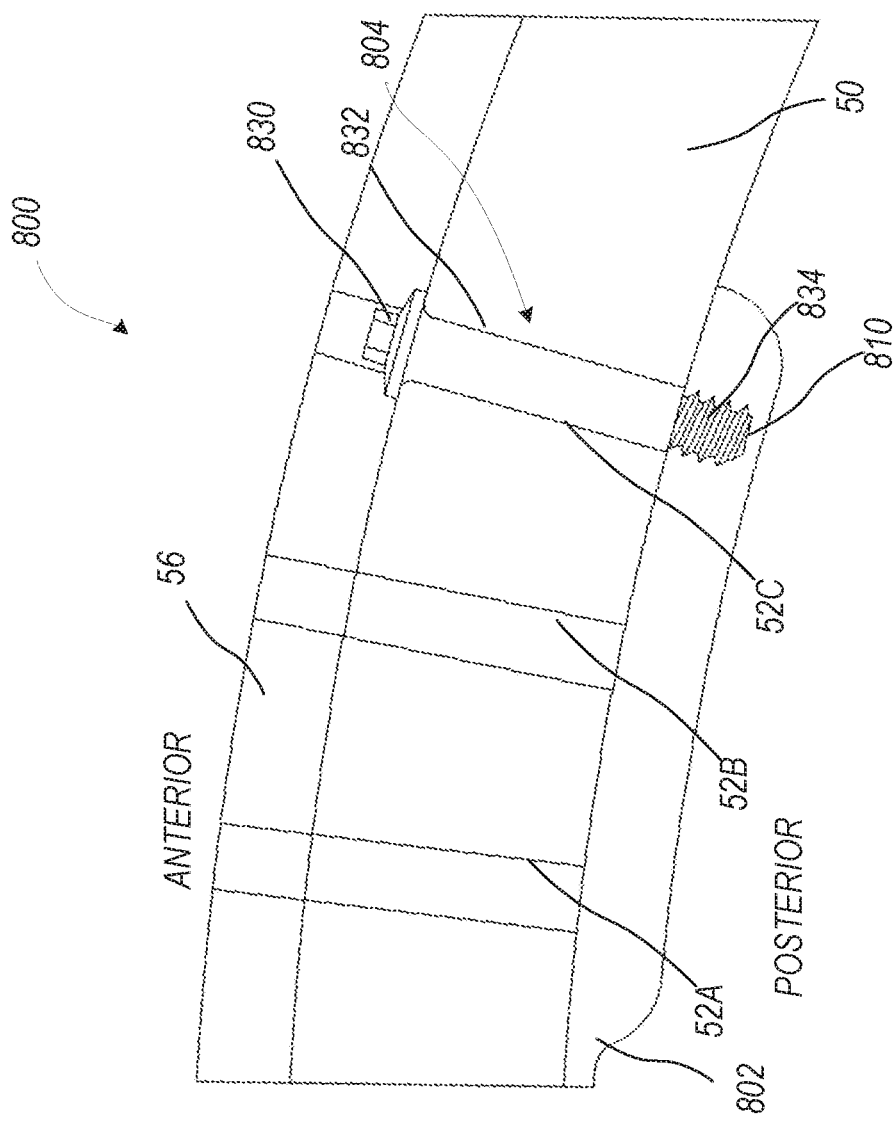
FIG. 8B shows an isometric view of an implant assembly, in accordance with an example of the present disclosure.
Figure 8A:
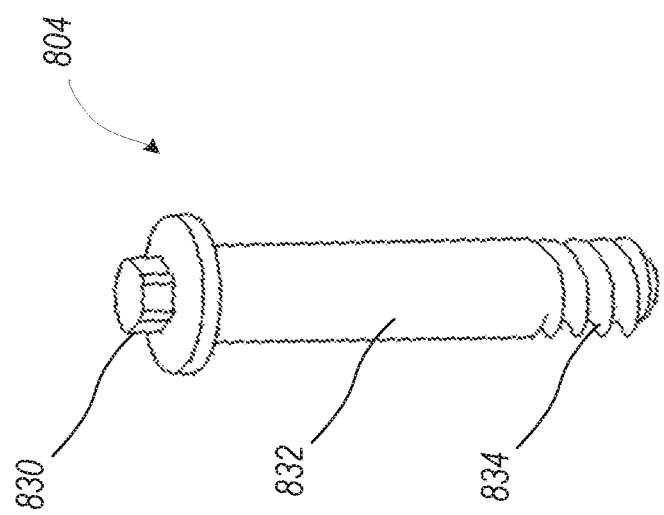
FIG. 8A shows an isometric view of a fastener of an implant assembly, in accordance with an example of the present disclosure.

FIG. 8A shows an isometric view of a fastener of an implant assembly, in accordance with an example of the present disclosure. Fastener 804 can include head 830, shank 832, and distal threaded portion 834.

In some examples, head 830 can include a tool interface, such as a hexagonal tool or bolt interface, in one example. Head 830 can be of a diameter larger than a bone bore, as discussed further below. Shank 832 can have a diameter smaller than the bone bore where shank 832 can also have a smooth finish to allow for shank 832 to be inserted through the bone bore with relatively little force or interaction between shank 832 and the bone bore.

Threaded portion 834 can include threads configured to interface with a bore of an implant, such as fine threads or machine threads. Threaded portion 834 can also have a diameter smaller than the bone bore to allow fastener 804 to be quickly inserted through the bone bore by minimizing interaction between threaded portion 834 and the bone bore. In some examples, fastener 804 can be similar to a lag bolt or shoulder bolt, but having shank and threaded portions with multiple diameters.

FIG. 8B shows an isometric view of an implant assembly, in accordance with an example of the present disclosure. Implant assembly 800 can include implant 802 and fastener 804. Also shown in FIG. 8B are rib portion 50 and skin portion 56, through which bores 52A-52C pass. Also shown in FIG. 8B are orientation indicators Posterior and Anterior.

Rib portion 50 and skin portion 56 can be a rib and skin of a patient. Rib bores 52A-52C can extend through skin portion 56 and rib portion 50 and can be created from the internal (posterior side) portion of the thoracic cavity, as discussed in further detail below.

Implant 802 can be similar to implant 300 discussed above, where implant 802 can include implant bore 810, which can extend from an anterior side of implant 802 partially into implant 802 and terminating prior to extending through implant 802 to posterior side of implant 802. In some examples, bore 810 can have a fine or machine thread configured to receive threaded portion 834 of fastener 804.

In operation of some examples, bores 52A-52C can be formed through rib portion 50 and skin portion 56. Implant 802 can then be aligned such that implant bore 810 aligns with rib bore 52C. Fastener 804 can then be inserted anterior to posterior into rib bore 52C until threaded portion 834 engages bore 810. Head 830 can then be engaged with a tool to rotate fastener 804, driving threaded portion 834 into bore 810 until head 830 makes contact with rib portion 50, preventing further anterior to posterior movement of fastener 804. In some examples, threaded portion 834 can include locking threads configured to prevent over-rotation of fastener 804 into bore 810 and to prevent back-out of fastener 804 from bore 810.

Because bore 810 does not extend through implant 802, the tip of fastener 804 does not protrude into the thoracic space, limiting edges exposed to internal organs and tissues. Also, because no cavity is exposed to the internal thoracic space, ingrowth can be reduced, which can reduce risk of infection. Implant 800 also reduces palpability by using blind bores (or is not exposed to an anterior portion of rib 50), such as bore 810, which allow implant 800 to be installed on the posterior portion of rib 50.

FIG. 9A shows an isometric view of fastener 904 of implant assembly 900, in accordance with an example of the present disclosure. FIG. 9B shows an isometric view of implant assembly 900, in accordance with an example of the present disclosure. FIGS. 9A and 9B are discussed below concurrently.

Implant assembly 900 can include implant 902 and fastener 904. Fastener 904 can include head 930, proximal threaded portion 932, and distal threaded portion 934. Also shown in FIG. 9B are rib portion 50 and skin portion 56, through which bores 52A-52C pass. Also shown in FIG. 9B are orientation indicators Posterior and Anterior.

In some examples, head 930 can include a tool interface, such as a hexagonal tool or bolt interface, in one example. Head 930 can be of a diameter smaller than bone bores 52A-52C. Proximal threaded portion 932 can have a minor diameter D2 smaller than a bone bore diameter D1 and a major diameter D3 can be larger than the bone bore diameter D1 and larger than head 930. Proximal threaded portion 932 can also have threads configured to engage bone, such as a coarse threading.

Distal threaded portion 934 can have a major diameter D4 that is smaller than the bone bore diameter D1, such that distal threaded portion 934 can pass through bone bore 52A with relatively little interaction with rib 50. Distal threaded portion 934 can include threads configured to interface with bore 910 of implant 902.

Rib portion 50 and skin portion 56 can be a rib and skin of a patient. Rib bores 52A-52C can extend through skin portion 56 and rib portion 50 and can be created from the internal (posterior side) portion of the thoracic cavity, as discussed in further detail below.

Implant 902 can be similar to implant 300 discussed above, where implant 902 can include implant bore 910, which can extend from an anterior side of implant 902 partially into implant 902 and terminating prior to extending through to posterior side of implant 902. In some examples, bore 910 can have a fine or machine thread configured to receive threaded portion 934 of fastener 904.

In operation of some examples, bores 52A-52C can be formed through rib portion 50 and skin portion 56. Implant 902 can then be placed against a posterior portion of rib 50 such that implant bore 910 aligns with rib bore 52C. Fastener 904 can then be inserted anterior to posteriorly into rib bore 52A until proximal threaded portion 932 engages rib bore 52A. Head 930 can then be engaged with a tool to rotate fastener 904, driving proximal threaded portion 932 into rib bore 52A in a self-tapping fashion, until distal threaded portion 934 reaches implant bore 910 at which point distal threaded portion 934 can be threaded into implant bore 910 until distal threaded portion 934 is fully threaded into implant bore 910. In some examples, distal threaded portion 934 can include locking threads configured to prevent over-rotation of fastener 904 into bore 910 and can prevent back-out of fastener 904 from implant bore 910.

Because major diameter D4 of distal threaded portion 934 has a diameter equal to or smaller than minor diameter D2 of first threaded portion 932, second threaded portion does not engage rib bore 52A, which can increase fastening time and operational efficiency. Because major diameter D3 can be larger than bone bore diameter D1 and larger than head 930, head 930 can be driven into the bone bore allowing fastener 904 to be driven into implant 902 until distal threaded portion 934 locks into implant bore 910. During fastening, major diameter D3 can self-tap into rib bore 52A.

FIG. 10A shows a posterior isometric view of implant 1000, in accordance with an example of the present disclosure. FIG. 10B shows an anterior isometric view implant 1000, in accordance with an example of the present disclosure. FIGS. 10A and 10B are discussed below concurrently.

Implant 1000 can include body 1001, tool interface region 1006 (or notch 1006), and bores 1010a-1010n. Body 1001 can include flat portion 1002 and curved portion 1004. In some examples, body 1001 can be malleable or bendable, such as at region 1006, to allow the body 1001 to better match a rib contour or profile. This bendability may be achieved because region 1006 is relatively thinner than the rest of body 1001, and/or because at least a portion of region 1006 is made of a different material than the rest of body 1001.

Implant 1000 can be similar to implant 300 discussed above, except that implant 1000 includes tool interface 1006, which can be a notch or a portion of curved portion 1004 having a reduced thickness. Notch 1006 can provide multiple functions, in some examples. For example, a placement tool can be coupled to tool interface 1006 as discussed in further detail below. Also, because notch 1006 has a relatively smaller thickness of curved portion 1004, body 1001 can be bent at notch 1006 to create a curved profile of implant 1000 to match a patient's anatomy. In one example, body 1001 can be bent at notch 1006 to align a curvature of flat portion 1002 with a curvature of a patient's rib.

Implant 1000 can also differ in that it can include friction element 1020. Friction element 1020 can extend outwardly from flat portion 1002. In some examples, friction element 1020 can be configured to engage a rib to help maintain a desired position of implant 1000 relative to the rib. In other examples, implant 1000 can include multiple friction elements. In some other examples, implant 1000 can include no friction element (such as friction element 1020), but can have an abrasive surface to minimize slipping of implant 1000 on a rib.

Figure 11:
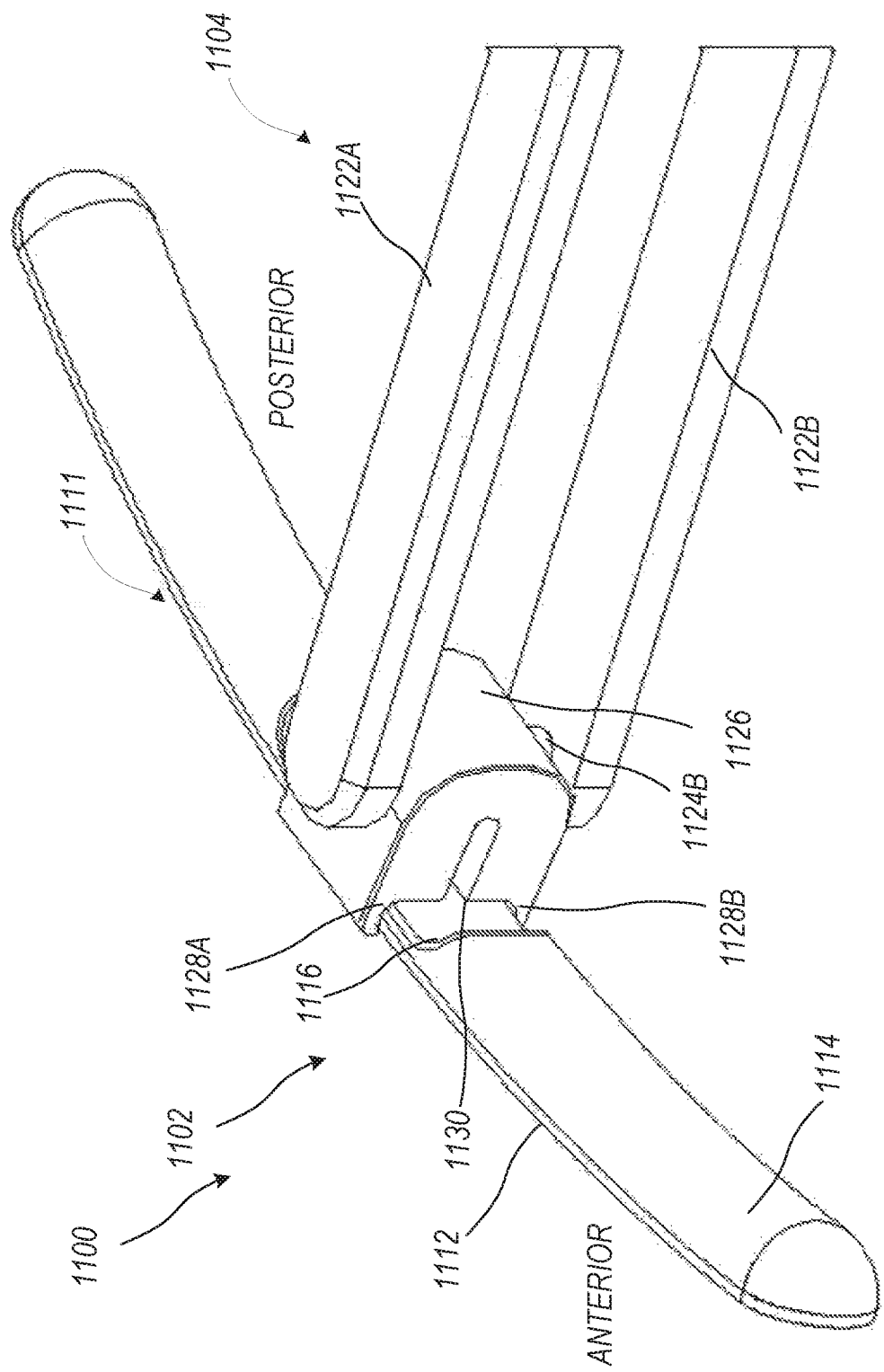
FIG. 11 shows an anterior isometric view of another implant assembly, in accordance with an example of the present disclosure.

FIG. 11 shows an isometric view of implant assembly 1100, in accordance with an example of the present disclosure. Implant assembly 1100 can include flat portion 1112, curved portion 1114, and tool interface 1116 (or notch 1116). Placement tool 1104 can include arms 1122A and 1122B, which can include pins 1124A and 1124B (only 1124B is shown in FIG. 11), respectively.

Implant 1100 can be similar to implant 1000 described above with respect to FIG. 10 and placement tool 1104 can be similar to either of placement tools 400 of FIG. 4A or 500 of FIG. 4B, except that placement tool 1104 includes coupler 1126. Coupler 1126 can include jaws 1128A and 1128B defining recessed portion 1130, where jaws 1128A and 1128B can flex such that they are configured to receive notch 1116 of implant 1102.

In some examples, coupler 1126 can include one or more bores configured to receive pins 1124A and 1124B to secure coupler 1126 to arms 1122A and 1122B, such that coupler 1126 is removably coupleable to tool 1104. Because coupler 1126 can be removable, one type of placement tool can be used for multiple types of implants, reducing cost. In other examples, coupler 1126 can be fixed to tool 1104, but can still pivot about pins 1124A and 1124B. In other examples, coupler 1126 can be rigidly secured to tool 1104. In other examples, coupler 1126 can be rotatably secured to tool 1104, but can be fixedly secured, such that coupler 1126 is not removable from tool 1104.

In operation of some examples, jaws 1128A and 1128B can engage tool interface 1126 and can couple thereto in a snap-fit configuration, in one example, allowing notch 1116 of implant 1102 to engage recess 1130. When implant 1102 contacts a rib, the reaction force from the rib can cause coupler 1126 to rotate about pins 1124A and 1124B rotating implant 1102 about tool 1104. This feature allows implant 1102 to be self-aligning with the rib, which can save time during an operation.

Figure 12:
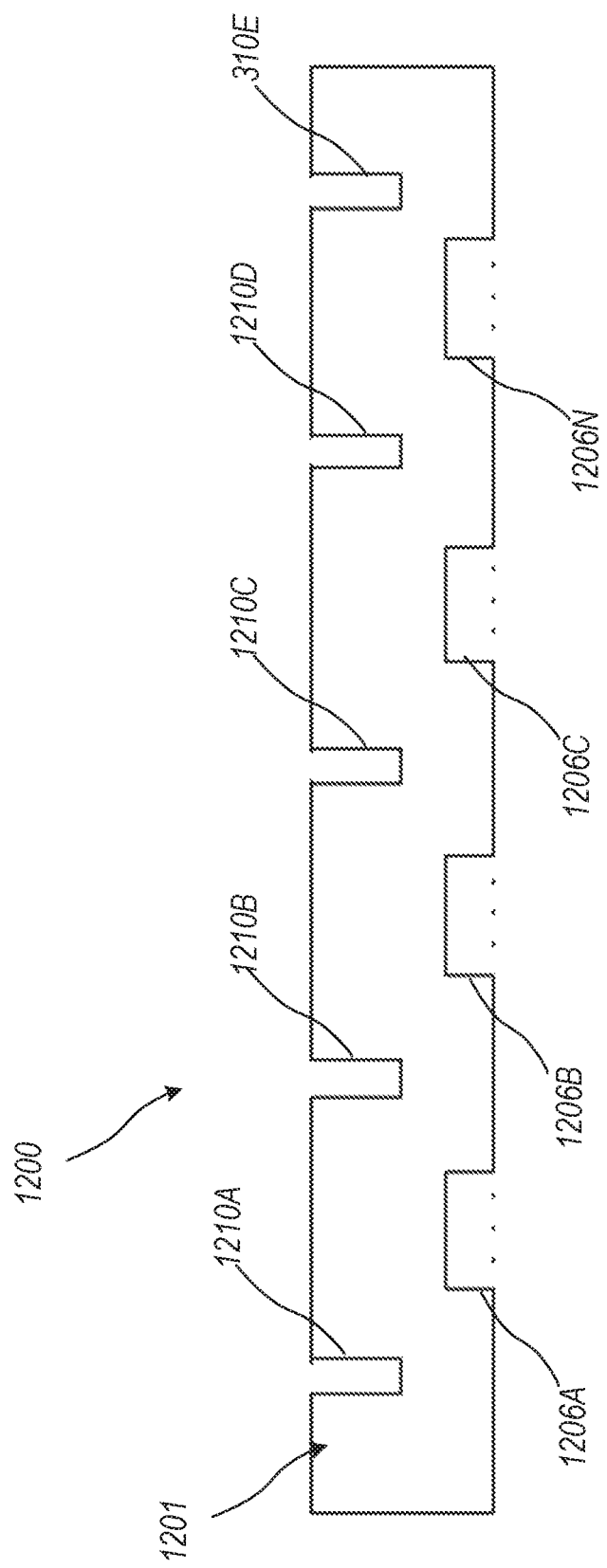
FIG. 12 shows a cross-sectional view of another implant, in accordance with an example of the present disclosure.

FIG. 12 shows a cross-sectional view implant 1200, in accordance with an example of the present disclosure. Implant 1200 can be similar to implant 1000, except that implant 1200 includes multiple notches 1206A-1206N.

Body 1201 of implant 1200 can include one, two, three, four, five, six, ten, and the like notches. Each of notches 1206A-1206N can have a relatively smaller thickness of body 1201 allowing body 1201 to be bent at any of notches 1206A-1206N such that a curvature of implant 1200 to be matched to patient-specific anatomy. In some examples, body 1201 can be bent at only one notch, such as notch 1206A, and in other examples, body 1201 can be bent at multiple notches, such as notches 1206A, 1206B, and 1206C.

Also, notches 1206A-1206N can provide multiple interfaces for a placement tool, such as tool 1104 of FIG. 11. In this way, a tool can be attached to any of notches 1206A-1206N as required for placement of implant 1200 along a posterior surface of a rib. For example, a placement tool can be placed at notch 1206a in some examples and 1206 in other examples. In some other examples, one placement tool can be placed at a first notch, such as notch 1206A, and another placement tool can be placed at a second notch, such as notch 1206C.

Figure 13:
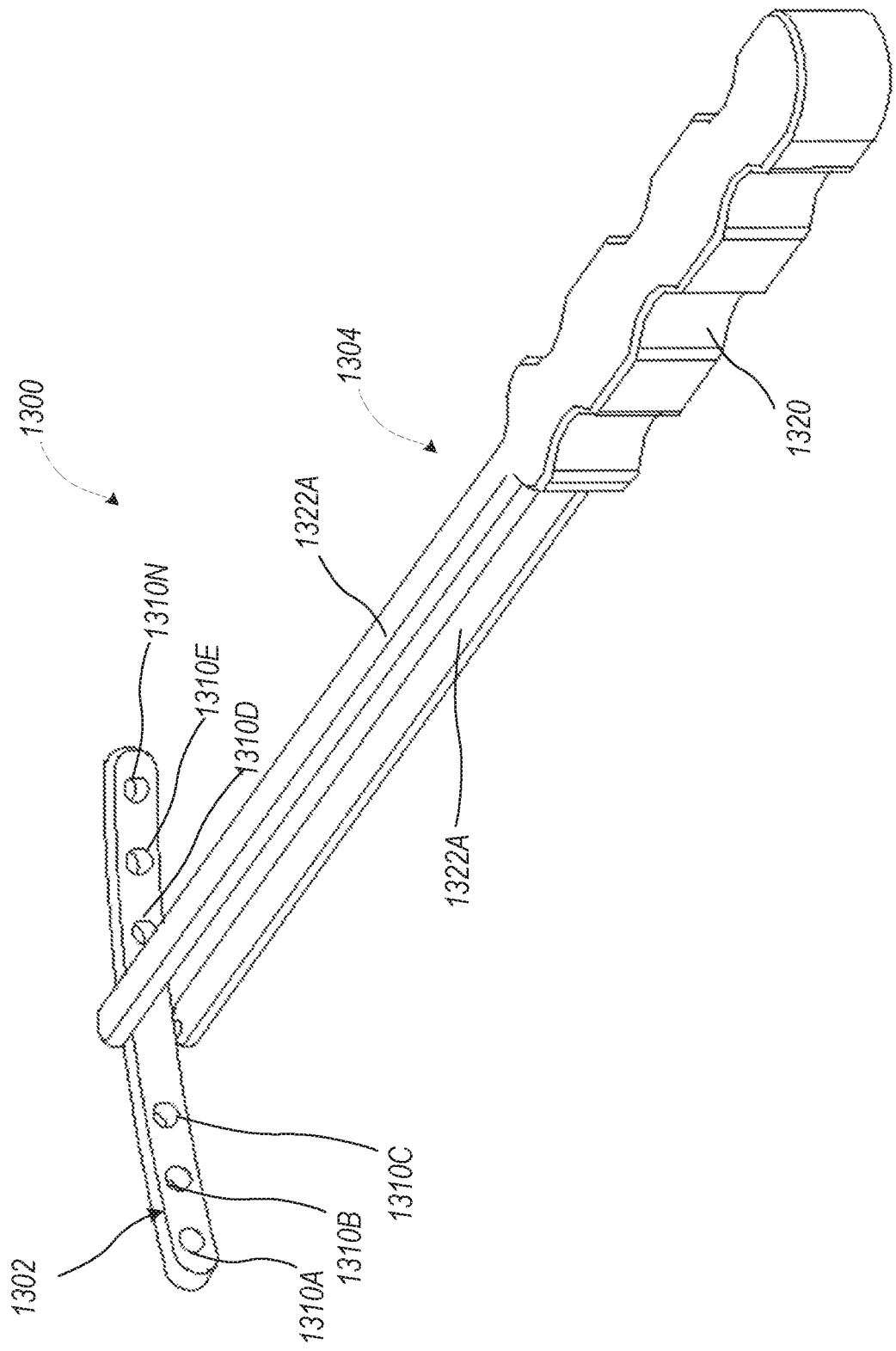
FIG. 13 shows an anterior isometric view of another implant assembly, in accordance with an example of the present disclosure.

FIG. 13 shows an anterior isometric view of implant assembly 1300, in accordance with an example of the present disclosure. Implant assembly 1300 can include template 1302 and placement tool 1304. In some examples, discussed further below, template 1302 can be a template or guide. In some examples, template 1302 can be malleable or bendable to match a rib contour or profile.

Template 1302 can be similar to implant 300, except that bores 1310A-1310N can extend through template 1302 such that a drill and/or fastener can pass through each of bores 1310A-1310N, allowing template 1302 to be used as a drilling guide or template for creating bores in ribs and skin.

Implant tool 1304 can interface with template 1302 such that template 1302 can pivot about the pins of implant tool 1304. Implant tool 1304 can be similar to implant tool 400 of FIG. 4; however, implant tool 500 of FIG. 5 can also be used to engage template 1302. Operations using implant tool 1304 and template 1302 are discussed in further detail below.

FIG. 14A shows an isometric view of a step of installing implant assembly 1300, in accordance with an example of the present disclosure. Implant assembly 1300 can include template 1302, tool 1304, and drill bit 1340. Template 1302 can include bores 1310A-1310N. Also shown in FIG. 14A are ribs 50A and 50B and skin portion 56.

In operation of one example, template 1302 can be secured to tool 1304 and template 1302 can be inserted into thoracic cavity, as discussed above with respect to FIG. 6, and template 1302 can be aligned on rib 50A. In some examples, a friction element can help maintain the position of template 1302 relative to rib 50A.

With template 1302 placed on the posterior side of rib 50A, drill bit 1340 can be passed through each of bores 1310A-1310N to create bores in rib 50A and adjacent skin portion 56. In some examples, template 1302 can serve only as a drill guide or template, helping to create bores in rib 50A and can be removed from the thoracic cavity thereafter. In other examples, template 1302 can also be used both as a drill guide and also as an implant.

Arms 1322A and 1322B can receive drill bit 1340 therebetween for drilling operations used to create bores in rib 50A. Also, when using template 1302 as a drill guide, handle 1320 of tool 1304 can be rotated to provide clearance for drill bit 1340 as drill bit is moved between bores 1310A-1310N. For example, handle 1320 can be rotated in direction R to provide clearance of operation of drill bit 1340 while creating a bore in rib 50a using bore 1310N of template 1302 as a guide.

FIG. 14B shows a top isometric view of the step of FIG. 14A of installing implant assembly 1300, in accordance with an example of the present disclosure. FIG. 14B is consistent with FIG. 14A, except that FIG. 14B shows bores 58a-58n in rib 50a. FIG. 14B also shows fracture 60 of rib 50A and shows how template 1302 can be positioned relative to fracture 60 such that bores 58A-58N can be created around fracture 60.

Figure 15A:
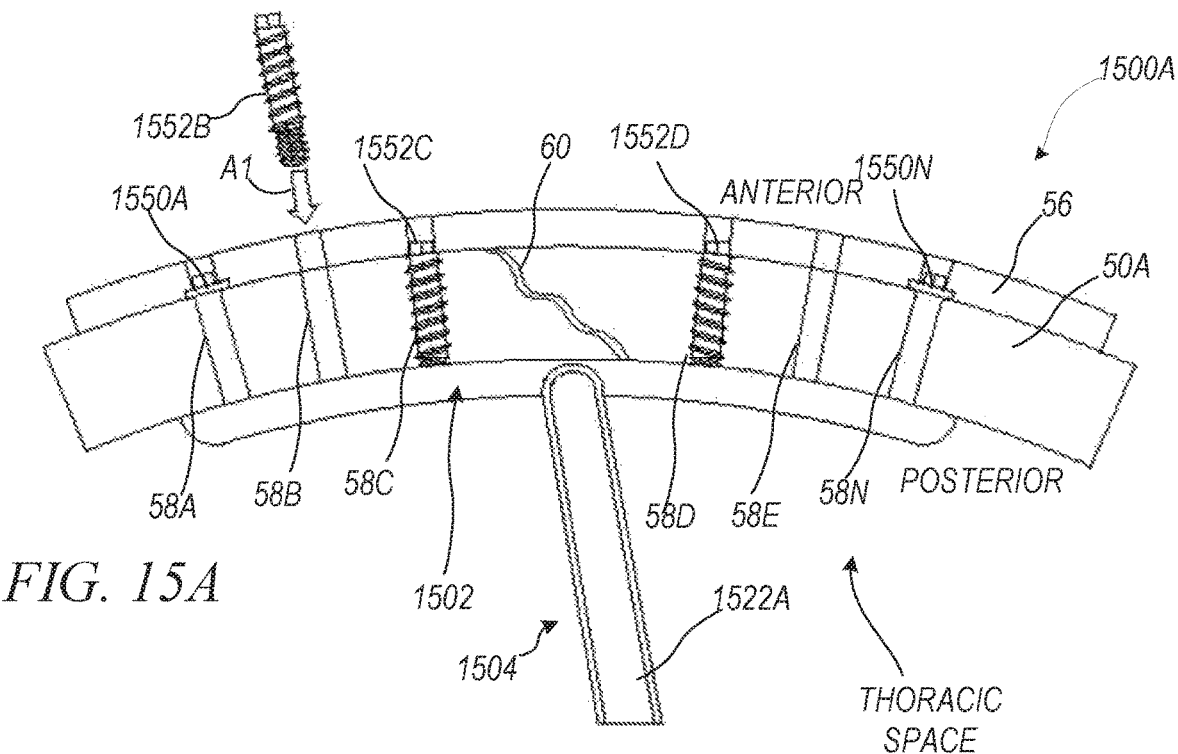
FIG. 15A shows a top isometric view of another step of installing an implant assembly, in accordance with an example of the present disclosure.

FIG. 15A shows a top isometric view of another step of installing implant assembly 1500A, in accordance with an example of the present disclosure. Implant assembly 1500 can include implant 1502, tool 1504, lag fasteners 1550A and 1550N and fasteners 1552B, 1552C, and 1552D. Also shown in FIG. 15A is rib 50A, skin portion 56, bone bores 58A-58N, and fracture 60.

The components of implant assembly 1500A can be consistent with those of the implant assemblies described above. FIG. 15A, though, further shows how fasteners can be used to secure implant 1502 to rib 50a.

Figure 15B:
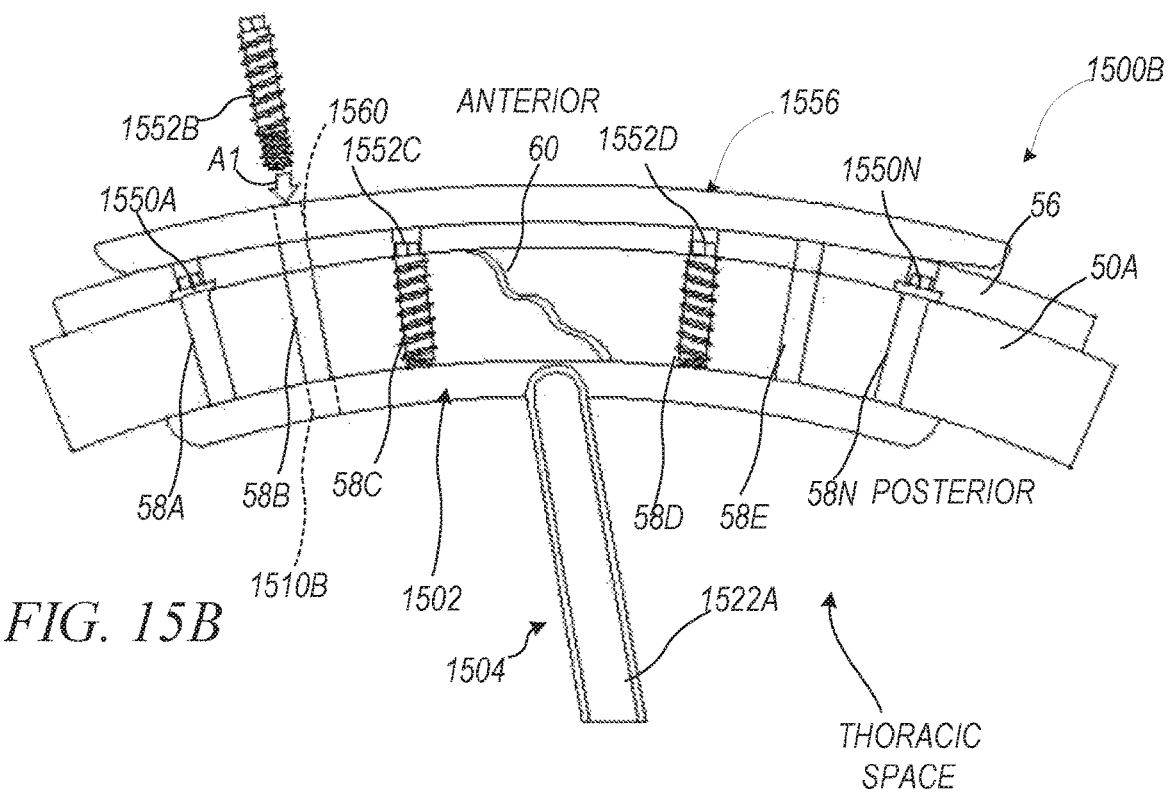
FIG. 15B shows a top isometric view of another step of installing an implant assembly, in accordance with an example of the present disclosure.

In operation of one example where template 1302 (shown in FIGS. 14A and 14B) can be used only as a guide. After template 1302 has been used to create bone bore 58a-58n, template (or guide) 1302 can be removed from the thoracic space and from placement tool 1304 or 1504. Implant 1502 can then be secured to placement tool 1504 and inserted into the thoracic space and placed against rib 50A, as shown in FIGS. 15A and 15B. Thereafter, in one example, lag fasteners 1550a and 1550N can be inserted into bone bores 58A and 58N from an anterior side of rib 50a and skin portion 56. Lag fasteners 1550A and 1550N can be inserted through rib 50a and can be secured to implant 1502 without engaging bores of rib 50A, to hold implant in position relative to rib 50A. In some examples, fewer lag fasters can be used such as one or none. In other examples, more lag fasters can be used, such as 3, 4, 5, or 6.

Once lag fasteners 1550A and 1550N are in place, fasteners 1552B-1552D can be inserted into bone bores 58B-58D, respectively, to threadably engage bone bores 58B-58D, until fasteners 1552B-1552D threadably engage implant bores (not shown) of implant 1502. Each fastener can then be torqued to a desired torque. Though not shown in FIG. 15A, bone bore 15E can receive either a lag fastener (similar to lag fastener 1550A) or a fastener having bone threads (similar to fastener 1552b).

FIG. 15B shows a top isometric view of another step of installing implant assembly 1500B, in accordance with an example of the present disclosure. Implant assembly 1500B can be the same as implant assembly 1500A, except that implant assembly 1500B can include placement guide 1556. In some examples, placement guide 1556 can include bores configured to align with bone bores 58A-58N and implant bores (only implant bore 1510B shown), through which fasteners can pass. In one example, shown in FIG. 15B, bore 1560 can align the placement of fastener 1552B with bone bore 58B and implant bore 1510B. In this way, guide 1556 can increase efficiency of securing fasteners to ribs and implants.

Because fasteners 1550A and 1550N and fasteners 1552B-1552D can be secured through rib bore 58A-58N external to the thoracic cavity, any debris produced by torqueing fasteners will be external to the thoracic cavity, potentially reducing complications caused by debris.

In another example, guide 1556 can be used as a drilling guide such that bone bores 58A-58N are created from an anterior side of the ribs, which can be helpful in procedures where drilling from a posterior side is not desirable or not possible.

Figure 16:
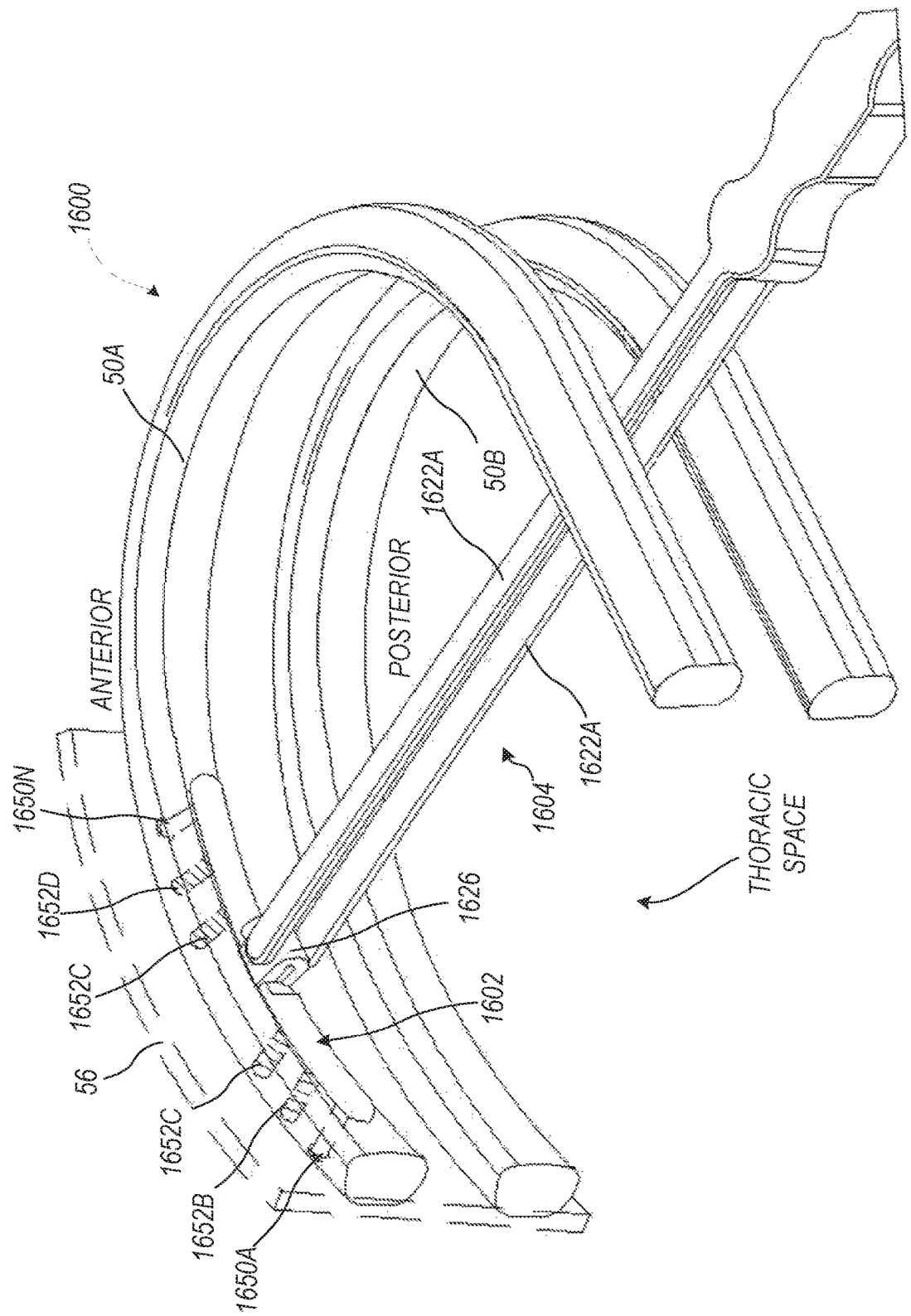
FIG. 16 shows an isometric view of another step of installing an implant assembly, in accordance with an example of the present disclosure.

FIG. 16 shows an isometric view of another step of installing implant assembly 1600, in accordance with an example of the present disclosure. Implant assembly 1600 can include implant 1602, placement tool, 1604, lag fasteners 1650a and 1650n, and fasteners 1652B-1652D.

As shown in FIG. 16, placement tool 1604 can include coupler 1626, similar to that of implant assembly 1100, discussed above. FIG. 16 shows all of lag fasteners 1650A and 1650N and fasteners 1652B-1652D securing implant 1602 to implant while coupler 1626 and placement tool 1604 hold implant 1602 against rib 50A. Once implant 1602 is sufficiently secured to rib 50A, coupler 1626 can be disengaged from implant 1602 and coupler 1626 and placement tool 1604 can be removed from the thoracic space.

Figure 17:
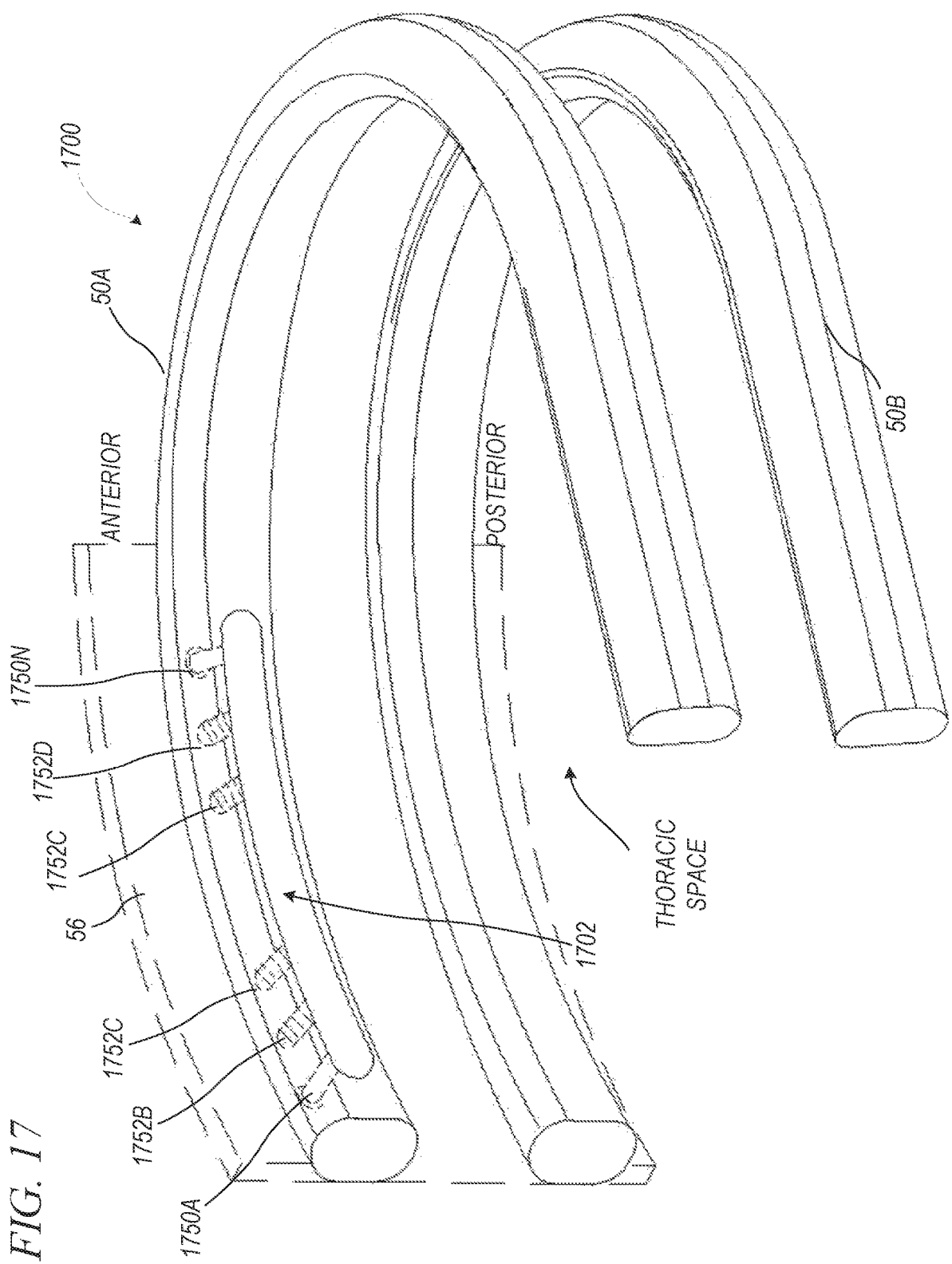
FIG. 17 shows an isometric view of a step of installing another implant assembly, in accordance with an example of the present disclosure.

FIG. 17 shows an isometric view of a step of installing implant assembly 1700, in accordance with an example of the present disclosure. FIG. 17 shows implant 1702 secured to rib 50a with the placement tool removed. Because implant assembly 1700 requires only a single posterior incision having a size relatively smaller than the size of the implant (such as implant 1702) and because implant assembly requires small openings or incisions for each fastener, the overall wound size can be reduced over one that may be required for installation of a plate from an anterior side of a rib. Also, because implant 1702 is within the thoracic space (posterior side of rib 50A), only fasteners 1750 are palpable from the anterior side of rib 50A, which can be less palpability than can exist with anteriorly installed rib plates.

Figure 18:
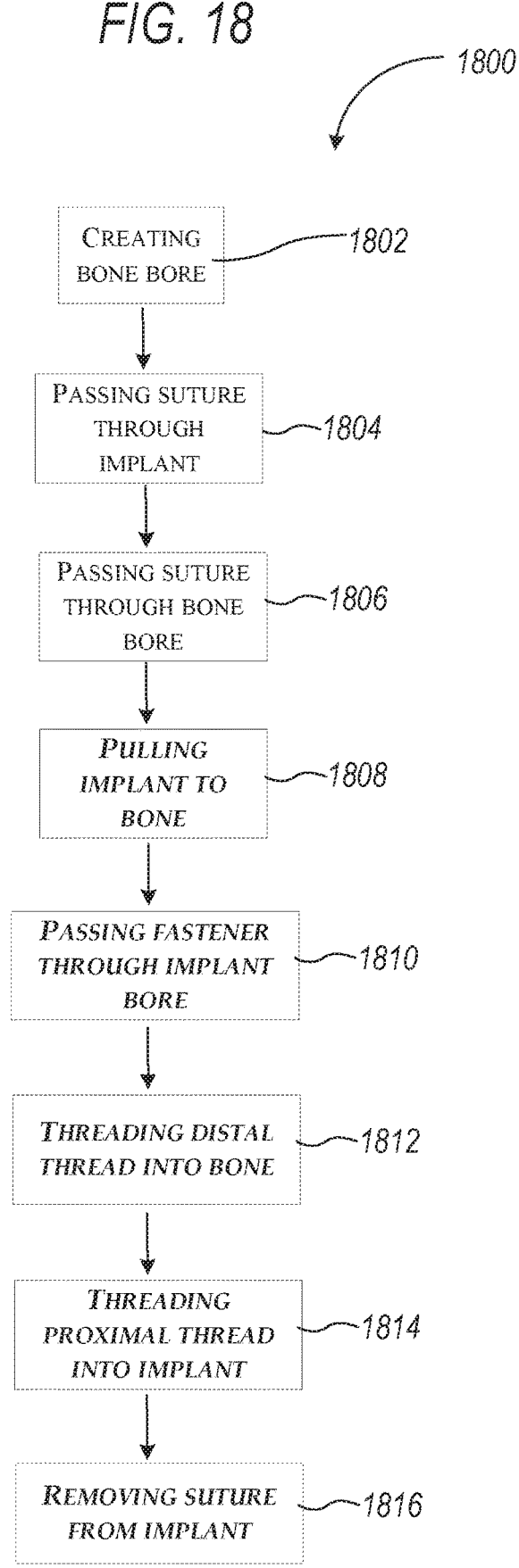
FIG. 18 shows a flow chart of a surgical procedure performed using a rib and sternal implant and tool, in accordance with an example of the present disclosure.

FIG. 18 shows a flow chart of method 1800, in accordance with an example of the present disclosure. The steps or operations of the method of FIG. 18 are illustrated in a particular order for convenience and clarity; many of the discussed operations can be performed in a different sequence or in parallel, and some operations may be excluded, without materially impacting other operations. The method of FIG. 18, as discussed, includes operations performed by multiple different actors, devices, and/or systems. It is understood that subsets of the operations discussed in the method of FIG. 18 attributable to a single actor, device, or system could be considered a separate standalone process or method.

In operation of one example, method 1800 can begin at step 1802 where a bone bore can be created. In one example, bore 52 can be created in rib 50, as shown in FIG. 1. At step 1804, sutures can be passed through an implant. In one example, sutures 108 can be passed through implant 102. At step 1806, sutures can be passed through the bone bore. In one example, sutures 108 can be passed through bore 52.

Then, at step 1808, the sutures can be used to pull the implant up to the bone. In one example, sutures 108 can be used to pull implant 102 up to rib 50. At step 1810, a driver or hand can be used to pass a fastener through the implant. In one example, driver 106 can pass fastener 104 through implant 102. Thereafter, the fastener can be threaded into bone at step 1812. In one example, fastener 104 can be threaded into rib 50 using driver 106. At step 1814, proximal threaded portion reaches implant 102, proximal threaded portion can be threaded into a bore of the implant. For example, a proximal threaded portion of fastener 104 can be threaded into bore 110A of implant 102. Once implant 102 is secure, the suture can be removed from the implant and rib bore. For example, suture 108 can be removed from implant 102 and rib bore 52.

FIG. 19 shows a flow chart of method 1900, in accordance with an example of the present disclosure. Method 1900 can begin with step 1902 where a placement tool can be attached to a template. In one example, placement tool 1304 can be attached to template 1302. At step 1904, the template can be pivoted or rotated to align with the placement tool. In one example, as shown in FIG. 13, template 1302 can be aligned with placement tool 1304. Then, at step 1906, the template and placement tool can be introduced or inserted through the incision and in the thoracic opening. For example, template 1302 and placement tool 1304 can be inserted into thoracic opening 54, as shown in FIG. 14A.

In some examples, before or after step 1904 and before step 1906, several steps can be performed on a patient. In some examples, an incision can be made on the opposite side of the fracture (on a posterior side of a patient) and in between a pair of ribs (typically a pair situated near the transverse plane of the fractured rib). From the incision (or through the oral cavity and trachea), and one or more tools can be used to deflate one or more of the patient's lungs. After the lungs have been deflated, organs near the fracture can be rested/nested below the fractured rib.

Once inserted, the template can be aligned with a bone or rib at step 1908 where the template can be used to gently push against the fractured rib to generate the contour of the rib. For example, template 1302 can be aligned with rib 50A. At step 1910 a drill bit or drill can be guided into position using a bore of the template. For example, drill bit 1340 can be guided to rib 50A using implant bore 1310N of template 1302. The drill bit can then be used to create a bore in the bone or rib, soft tissue, and skin using the template as a guide at step 1912. For example, drill bit 1340 can be used to create bore 58N in rib 50A using template 1302 as a guide.

After drilling, the guide and placement tool can be removed from the thoracic opening and the guide can be removed from the placement tool at step 1914. Then, an implant can be attached to the placement tool at step 1916. In some examples, prior to attaching the implant to the placement tool, the surgeon can bend the implant to match the contour generated with the template. For example, implant 602 can be bent to match template 1302 and can then be attached to placement tool 604. At step 1918, the implant can be pivoted or rotated to align with the placement tool. In one example, as shown in FIG. 6, implant 602 can be aligned with placement tool 604. Then, at step 1920, the implant and placement tool can be inserted into a thoracic opening. For example, implant 602 and placement tool 604 can be inserted into thoracic opening 54. In some examples, the placement tool can then be used to hold the implant against the fractured rib.

At step 1922, fasteners can be threaded into the bone bores and the implant bores from the outside of the patient and through the drilled holes until they engage and lock with the implant. For example, lag fasteners 1550A and 1550N and fasteners 1552B-1552D can be inserted into rib bores 58A-58N. At step 2024, the placement tool can be detached from the implant. For example, placement tool 1604 can be detached from implant 1602. At step 1926, the placement tool can be removed from the thoracic opening and the procedure can be completed. For example, placement tool 1604 can be removed from the thoracic cavity through the posterior incision, leaving behind implant 1602 secured to rib 50A. In some examples, additional fasteners can be secured to the implant after the placement tool is removed from the thoracic cavity. After removal of the plate holding implant, the organs can be replaced, the lungs can be inflated and the incision(s) can be closed. Because the implant can be secured within the thoracic space (on a posterior side of the rib), only the fasteners are palpable from the anterior side of rib 50A, which can be less palpable than can exist with anteriorly secured rib plates. Further, because the drill creates the openings on the anterior side of the patient's ribcage, only small openings must be closed on the anterior portion of the patient, helping to reduce scarring on the anterior side of the patient's rib cage.

In some examples, methods 1800 and/or 1900 can be performed multiple times for attachment of multiple implants to multiple ribs or to span multiple fractures on the same rib. Each method can be followed by any other of the methods.

ADDITIONAL NOTES

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. An implant assembly for securing an implant to a human rib, the implant assembly comprising:
   an implant securable to a human rib, the implant comprising:
      an elongate body comprising:
         a first portion and a second portion opposite the first portion;
         an implant bore extending through the first portion and partially into the second portion; and
         a placement tool interface extending into the body;
   a placement tool comprising:
      a handle;
      an arm extending from the handle;
      a second arm extending from the handle with the first arm; and
      a retaining pin extending from a distal portion of the arm, the retaining pin engageable with the placement tool interface to form a pivotable engagement therewith to allow the implant to rotate about the retaining pin between an orientation perpendicular to the arm and the second arm and an orientation parallel to and between the arm and the second arm; and
   a fastener comprising:
      a proximal threaded portion securable to the rib; and
      a distal threaded portion extending distally from the proximal threaded portion, the distal threaded portion threadably securable to the implant bore.

2. The implant assembly of claim 1, the assembly further comprising:
   a lag screw configured to pass through a rib bore without threadably engaging the rib bore and including a lag distal threaded portion threadably securable to a second bore of the implant.

3. The implant assembly of claim 1, wherein the fastener further comprises:
   a head comprising a tool interface, the head including a head diameter; and
   a body extending distally from the head, the body comprising:
      the proximal threaded portion that extends distally from the head, the proximal threaded portion comprising:
         a proximal minor diameter that is larger than the head diameter; and
         a proximal major diameter; and
      the distal threaded portion that extends distally from the proximal threaded portion, the distal threaded portion comprising:
         a distal major diameter of a size equal to or smaller than the proximal minor diameter.

4. The implant assembly of claim 3, wherein the distal threaded portion further comprises:
a locking thread adjacent the proximal threaded portion, the locking thread configured to lockably engage one of the implant bore including a first thread type.

5. The implant assembly of claim 4, wherein the second arm is coupled to a distal portion of the handle, the first and second arms extending distally from the elongate handle, the first and second arms movable between a first position and a second position.

6. The implant assembly of claim 5, wherein the placement tool further comprises:
a second retaining pin extending from a distal portion of the second arm towards the first arm such that the first retaining pin is spaced away from the second retaining pin, the second retaining pin coaxial with the first retaining pin when the first and second arms are in a first position, the first retaining pin and second retaining pin spaced further apart when the first and second arms are in a second position.

7. The implant assembly of claim 6, wherein the placement tool interface further comprises:
a first pin bore extending into thy: second portion, the first bore configured to receive the first retaining pin; and
a second pin bore coaxial with the first pin bore and configured to receive the second retaining pin.

8. The implant assembly of claim 7, wherein the first pin bore and second pin bore terminate in the second portion prior to intersecting.

9. The implant assembly of claim 1, wherein:
the first portion includes a flat outer face, the elongate body curved along a plane perpendicular to the flat outer face; and
the second portion extends from the first portion to form a curved outer face.

10. The implant assembly of claim 9, wherein the implant further comprises:
a plurality of bores extending through the flat outer face and partially into the second portion, each of the plurality of bores capable of receiving the fastener.

11. The implant assembly of claim 9, the second portion further comprising:
a notch in the curved outer face located at the placement tool interface and configured to allow the elongate body to be bent at the notch.

12. An implant assembly for securing an implant to a human rib, the implant assembly comprising:
an implant securable to a human rib, the implant comprising:
an elongate body including:
a first portion and a second portion opposite the first portion;
an implant bore extending through the first portion and partially into the second portion; and
a placement tool interface extending into the body; and
a placement tool comprising:
a handle;
an arm extending from the handle; and
a retaining pin extending from a distal portion of the arm, the retaining pin positionable within the placement tool interface to allow the implant to rotate about the retaining pin with respect the arm.

13. The implant assembly of claim 12, wherein:
the first portion includes a flat outer face, the elongate body curved along a plane perpendicular to the flat outer face; and
the second portion extends from the first portion to form a curved outer face.

14. The implant assembly of claim 13, wherein the implant further comprises:
a plurality of bores extending through the flat outer face and partially into the second portion, each of the plurality of bores capable of receiving the fastener.

15. An implant assembly for securing an implant to a human rib, the implant assembly comprising:
an implant securable to a human rib, the implant comprising a body including a first portion and a second portion opposite the first portion, the body defining an implant bore extending through the first portion and partially into the second portion, and the body further defining a placement tool interface extending into the body; and
a placement tool comprising:
a handle;
a first arm and a second arm each extending from the handle; and
a retaining pin extending from a distal portion of the first arm, the retaining pin engageable with the placement tool interface to allow the implant to rotate 360 degrees between the first arm and the second arm about the retaining pin.

16. The implant assembly of claim 15, wherein:
the first portion includes a flat outer face, the elongate body curved along a plane perpendicular to the flat outer face; and
the second portion extends from the first portion to form a curved outer face.

17. The implant assembly of claim 16, the second portion further comprising:
a notch in the curved outer face located at the placement tool interface and configured to allow the elongate body to be bent at the notch.

* * * * *

UNITED STATES PATENT AND TRADEMARK OFFICE
CERTIFICATE OF CORRECTION

| | |
|---|---|
| PATENT NO. | : 10,918,428 B2 |
| APPLICATION NO. | : 16/183141 |
| DATED | : February 16, 2021 |
| INVENTOR(S) | : Garcia et al. |

Page 1 of 1

It is certified that error appears in the above-identified patent and that said Letters Patent is hereby corrected as shown below:

In the Claims

In Column 19, Line 23, in Claim 7, delete "thy:" and insert --the-- therefor

Signed and Sealed this
Fifteenth Day of February, 2022

Drew Hirshfeld
*Performing the Functions and Duties of the
Under Secretary of Commerce for Intellectual Property and
Director of the United States Patent and Trademark Office*